(12) United States Patent
Masahiro et al.

(10) Patent No.: US 9,859,511 B2
(45) Date of Patent: Jan. 2, 2018

(54) ORGANOIRIDIUM COMPLEX FOR ORGANIC ELECTROLUMINESCENT ELEMENTS

(71) Applicants: Tanaka Kikinzoku Kogyo K.K., Tokyo (JP); Osaka Prefecture University Public Corporation, Osaka (JP)

(72) Inventors: Yasushi Masahiro, Tokyo (JP); Shigeyuki Yagi, Osaka (JP); Junichi Taniuchi, Ibaraki (JP)

(73) Assignees: TANAKA KIKINZOKU KOGYO K.K., Tokyo (JP); OSAKA PREFECTURE UNIVERSITY PUBLIC CORPORATION, Osaka (JP)

( * ) Notice: Subject to any disclaimer, the term of this patent is extended or adjusted under 35 U.S.C. 154(b) by 0 days.

(21) Appl. No.: 15/502,695

(22) PCT Filed: Aug. 26, 2015

(86) PCT No.: PCT/JP2015/073939
§ 371 (c)(1),
(2) Date: Feb. 8, 2017

(87) PCT Pub. No.: WO2016/031840
PCT Pub. Date: Mar. 3, 2016

(65) Prior Publication Data
US 2017/0237021 A1 Aug. 17, 2017

(30) Foreign Application Priority Data

Aug. 28, 2014 (JP) .................................. 2014-173756

(51) Int. Cl.
*C07F 15/00* (2006.01)
*H01L 51/50* (2006.01)
*H01L 51/00* (2006.01)
*C09K 11/06* (2006.01)

(52) U.S. Cl.
CPC ...... *H01L 51/0085* (2013.01); *C07F 15/0033* (2013.01); *C09K 11/06* (2013.01); *C09K 2211/1007* (2013.01); *C09K 2211/1011* (2013.01); *C09K 2211/1029* (2013.01); *C09K 2211/185* (2013.01); *H01L 51/5016* (2013.01)

(58) Field of Classification Search
CPC .............................. C07F 15/00; H01L 51/50
USPC ............................................. 546/2; 313/504
See application file for complete search history.

(56) References Cited

FOREIGN PATENT DOCUMENTS

JP 2005035902 A 2/2005
JP 2008222635 A 9/2008
WO WO 2005118606 A1 12/2005

OTHER PUBLICATIONS

K. Noine, et al. Red Phosphorescent Iridium Complexes having a Bulky Ancillary Ligand for Solution-processed Organic Light Emmitting Diodes. Journal of Photopolymer Science and Technology, 2008, vol. 21, No. 2, pp. 323-325.
S. Ikawa, et al. Photoluminescence color tuning of phosphorescent bis-cyclometalated iridium(III) complexes by ancillary ligand replacement. Dyes and Pigments, 2012, vol. 95, pp. 695-705.

*Primary Examiner* — Charanjit Aulakh
(74) *Attorney, Agent, or Firm* — Orrick, Herrington & Sutcliffe LLP; Joseph A. Calvaruso

(57) ABSTRACT

The present invention provides an organometallic complex having a high quantum efficiency even in a polymer thin film as a emitting material for organic electroluminescent (EL) element. The present invention relates to an organoiridium complex for an organic electroluminescent element represented by the following Formula; wherein a C—N ligand including two atomic groups ($A^1$, $A^2$), and a β-diketone ligand in line symmetry having two tert-butyl-substituted phenyl groups are coordinated with an iridium atom. The organoiridium complex of the present invention has a high quantum efficiency even in a polymer thin film with respect to green to yellow electroluminescence.

[Chemical Formula 1]

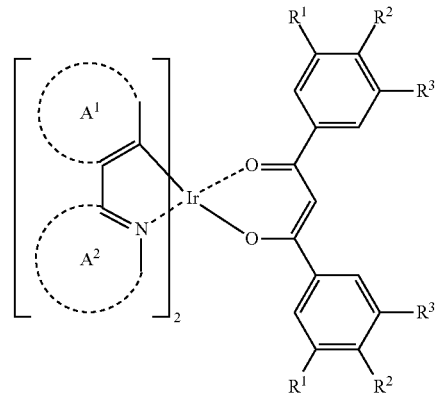

(In the aforementioned Formula, $R^1$, $R^2$, and $R^3$ are each a tert-butyl group or a hydrogen atom, and have at least one tert-butyl group; they may bond each other to thereby form a saturated hydrocarbon ring, when having two tert-butyl groups; $A^1$, $A^2$ are each an unsaturated hydrocarbon ring, at least one is a single ring, and at least one is a heterocyclic ring).

7 Claims, 4 Drawing Sheets

ORGANOIRIDIUM COMPLEX FOR ORGANIC ELECTROLUMINESCENT ELEMENTS

TECHNICAL FIELD

The present invention relates to a technique that provides an organoiridium complex suitable as an organic electroluminescent (EL) element, and particularly relates to an organoiridium complex useful as a green to yellow emitting material.

BACKGROUND ART

Technical development of the organic electroluminescent (EL) element is expected as next-generation displays and lighting. The features have advantages of low energy consumption, being capable of making thinner, excellent response speed, being capable of clear image display in both dark and bright places, and the like.

The basic structure of the organic EL element is a sandwich-like structure in which an organic compound of sole layer or multiple layers is sandwiched by a pair of electrodes. Specifically, there is proposed an element having a structure which uses, as a main configuration, a sandwich structure of a cathode/electron transport layer/emission layer/positive hole transport layer/anode/glass substrate, and which is obtained by appropriately adding a positive hole (electron) injection layer, buffer layer, interlayer insulating film, and the like in order to further enhance the properties. The emission layer which is a center of the sandwich structure uses various emitting materials, and the properties of the emission layer are required to easily flow electrons and positive holes which are transported from the cathode and anode, to have excellent light emission efficiency, to be durable, and the like.

Because of those demanded properties, development of phosphorescent materials has been required instead of the fluorescent materials having been conventionally applied as the emitting materials for the organic EL element. Since a generation probability ratio of excited molecule of an excited singlet to that of an excited triplet is 1:3 in the organic EL element, the phosphorescent material which exhibits phosphorescence by transition from the excited triplet state to the ground state is focused on in contrast to the fluorescent material which emits light by transition from the excited singlet to the ground state. Various organometallic complexes have been developed as such phosphorescent materials, and for example, there has been proposed an organometallic complex, as represented by the following Formula, in which a ligand (C—N ligand) having a heterocyclic ring and a C—N structure, and a ligand such as β-diketone are coordinated with a metal atom such as platinum or iridium. Specifically, PTL 1 discloses an organoiridium complex having a ligand with two benzene rings (diphenyl diketone) as the β-diketone ligand ($SO_2$, etc. in PTL 1). In addition, PTL 2 discloses an organoplatinum complex or the like having a ligand with two butoxy-substituted benzene rings (tetra-butoxydiphenyl diketone) as the β-diketone ligand (PTL 2, Formula [1-1]). The light emission efficiency of the organometallic complexes described in the aforementioned PTLs is enhanced by application of the ligands having benzene ring as the β-diketone ligand.

[Chemical Formula 1]

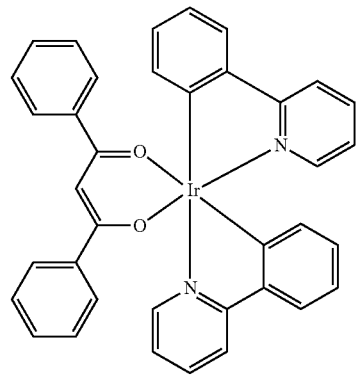

Patent literature 1

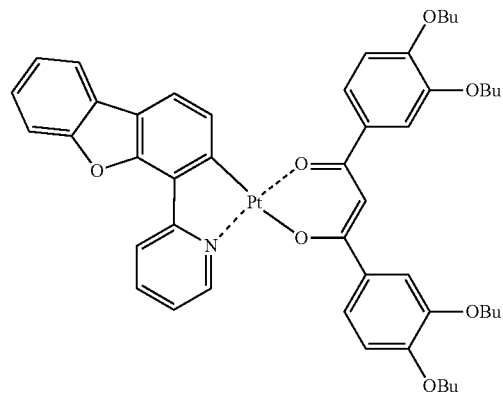

Patent literature 2

CITATION LIST

Patent Literature

PTL 1: Japanese Patent Laid-Open Publication No. 2005-35902

PTL 2: Japanese Patent Laid-Open Publication No. 2008-222635

SUMMARY OF INVENTION

Technical Problem

Incidentally, "current efficiency (cd/A)" and "quantum efficiency (%)" are known as a basis for evaluating the light emission efficiency of the organic EL element. The current efficiency exhibits a luminance (or light strength considering visibility) with respect to an amount of current per unit, whereas the quantum efficiency is a percentage of the number of photons capable of being taken out as light energy with respect to an electric power consumption (the number of the injected carriers). In the quantum efficiency, there can be eliminated a part of consumed power which cannot be emitted as light energy (for example, a part of loss due to resistance), of the consumed power. Therefore, when evaluating the light emission efficiency by the quantum efficiency rather than the current efficiency, it is possible to evaluate the light emission efficiency of the organic EL element as a value close to the actual efficiency. Under these circumstances, when considering the organometallic complexes described in PTLs 1 and 2, the complexes do not necessarily have high quantum efficiency although there has been examined the complexes having high current efficiencies as the light emission efficiency.

In addition, it is effective that the aforementioned quantum efficiency shows a high value in a polymer (solid) such as a thin film. The reason is that usually an organometallic complex is not introduced in a solution or solvent, but is doped in a polymer thin film and is utilized as a emission layer in implementation to the organic EL element. In this point, many of the organometallic complexes described in PTLs 1 and 2, etc. showed a quantum efficiency to a certain degree in the solution of the organic solvent and the like, but the quantum efficiency was lowered in the polymer (solid) such as a thin film in many cases, and thus those did not show a high quantum efficiency in the thin film.

Accordingly, the present invention is aimed at providing an organometallic complex that has high quantum efficiency even in a (polymer) thin film as a emitting material for the organic EL element, and particularly provides an organometallic complex which can produce an organic EL element having high quantum efficiency with respect to a green to yellow electroluminescence.

Solution to Problem

For solving the aforementioned problems, the present inventors have focused on an organoiridium complex having iridium as a center atom. Although platinum complexes have also been developed as the organometallic complexes as described in PTL 2, the platinum complex has a high flatness and has an unoccupied ligand in the platinum atom that is the center element, and thus energy loss is easily generated. Specifically, the platinum complex is affected by various interactions including: intermolecular interaction (so-called self-organization) such as association-excimer formation; interaction with a medium such as solvents or matrix (mother materials); furthermore, association with other coexisting molecules; and the like. On the other hand, in the organoiridium complex, since the three ligands have a steric conformation, the aforementioned various interactions as in the platinum complex are not generated, and the energy loss is not easily caused, and thus it is considered that a material having high quantum efficiency is easily obtained.

Moreover, with respect to the quantum efficiency, attention has been focused on a "photoluminescence (PL) quantum yield" of the emitting material which is one of the factors that determines the quantum efficiency. When the quantum efficiency is roughly divided into "external quantum efficiency" and "internal quantum efficiency", this PL quantum yield is, as shown in the following equations, one of the factors that determine the internal quantum efficiency. High internal quantum efficiency is required for the emitting materials, and particularly, influences of "exciton generation efficiency" and "PL quantum yield" are large as the factor that determines the internal quantum efficiency. Among them, since the "exciton generation efficiency" is determined depending on the difference in a fluorescent material and a phosphorescent material, the height of the PL quantum yield is important in order to enhance the internal quantum efficiency. Note that carrier balance in the following equation is a factor determined by combination of the materials and element structure such as film thickness control.

[Quantum Efficiency]

External quantum efficiency=(Efficiency of light extraction)×Internal quantum efficiency Internal quantum efficiency=(Exciton generation efficiency)×(PL quantum yield)×(Carrier balance)

Accordingly, the present inventors have intensively studied organoiridium complexes showing a high photoluminescence (PL) quantum yield particularly in the polymer thin film. In the way of the study, the inventors have focused on organoiridium complexes which generate so-called "rigidchromism" where the emitted light in the polymer thin film is changed to be different from the emitted light in a solvent of solution, and have found that some complexes which generate such a rigidchromism show a high photoluminescence quantum yield in the polymer thin film, and then have completed the present invention. Here, the "chromism" means a phenomenon that optical properties of a substance are changed reversibly by an external stimulation. The "rigidchromism" indicates the case that the external stimulation which induces the chromism depends on the kind of the medium molecule, and the color of the emitted light is changed depending on whether the medium molecule is solution or solid. On the basis of the above studies, the present inventors have completed the present invention as an organoiridium complex which generates the rigidchromism.

Namely, the present invention relates to an organoiridium complex for an organic electroluminescent element represented by the following Formula; wherein a C—N ligand including two atomic groups ($A^1$, $A^2$), and a β-diketone ligand in line symmetry having two tert-butyl-substituted phenyl groups are coordinated with an iridium atom.

[Chemical Formula 2]

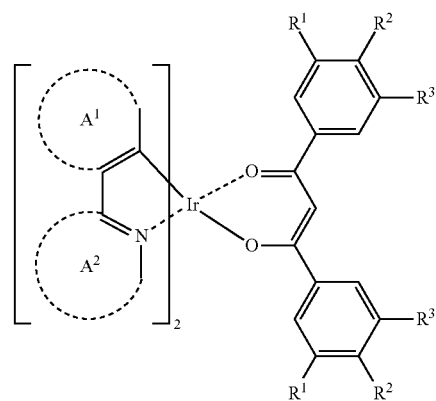

(In the aforementioned Formula, $R^1$, $R^2$, and $R^3$ are each a tert-butyl group or a hydrogen atom, and have at least one tert-butyl group; they may bond each other to thereby form a saturated hydrocarbon ring, when having two tert-butyl groups; $A^1$ and $A^2$ are each an unsaturated hydrocarbon ring, at least one is a single ring, and at least one is a heterocyclic ring.)

The primary feature of the present invention is that, while assuming that the β-diketone as a ligand has a phenyl group and is in line-symmetry, it further has tert-butyl group as a substituent. An organoiridium complex having such a β-diketone tends to have a high photoluminescence quantum yield. However, even in the organoiridium complex having such a tert-butyl group, when a surrounding medium molecule was a solid polymer thin film, the quantum efficiency was not always to be high. As a result of further study by the present inventors as to the organoiridium complex having a high photoluminescence quantum yield even in the polymer thin film, the present invention has been completed by employing the following structure as the C—N ligand. On the other hand, for the design of the structure of an organometallic complex in the conventional techniques, the C—N ligand may be optionally selected from many mentioned structures as long as the desired luminescent color (red, blue, green, etc.) can be emitted, mainly in consideration of the wavelength sift. Namely, in the conventional technique, only the structure of β-diketone was characterized with almost no limitation of the C—N ligand.

As explained above, according to the present invention, the aforementioned β-diketone ligand is employed and, at the same time, the C—N ligand is also limited to the ligand having the following structure. When providing the organoiridium complex having a high photoluminescence quantum yield even in the polymer thin film, the present inventors have thought that the reason why the structure of the C—N ligand is to be specified is that the light emitting excited state of the iridium complex having a high photoluminescence quantum yield in the thin film is based on the charge transfer transition from the O—O ligand to the C—N ligand, and the C—N ligand preferably has a structure having a high electron accepting property. Here, when the polarity of the iridium complex is different between ground state and excited state, it is one factor of rigidchromism that the energy level (band gap) ΔE varies by the influences of the surrounding medium molecule. And, when creating the excited state of a charge transfer type by the aforementioned electron accepting C—N ligand, the rigidchromism may be realized. As a result, the present inventors have thought that an organoiridium complex, which makes the photoluminescence quantum yield varying with ΔE in the thin film high, would be available.

From the above studies, the present inventors have completed the present invention which is an organoiridium complex having a high photoluminescence quantum yield particularly in the thin film by specifying not only the feature of the β-diketone ligand but also the kind of the structure of the C—N ligand. The rigidchromism occurred in the organoiridium complex of the present invention is that in a peak of emission spectrum, a wavelength ($\lambda_{PL}$) in the polymer thin film shifts more to the short wavelength side, than a wavelength ($\lambda_{PL}$) in an organic solvent. When the wavelength shift ($\Delta\lambda_{PL}$) due to this rigidchromism is 15 nm or more and 100 nm or less, the organoiridium complex tends to have a particularly high light emission quantum efficiency. Further, the $\Delta\lambda_{PL}$ is particularly preferably 25 nm or more and 60 nm or less.

Hereinafter, the organoiridium complex of the present invention will be explained in detail.

The organoiridium complex of the present invention is obtained by coordinating the two C—N ligands and the β-diketone with the trivalent iridium atom. The two C—N ligands have the same structure, and the β-diketone has the line-symmetrical structure. The specific structures of the C—N ligand and the β-diketone ligand will be explained below.

The β-diketone ligand applied to the present invention is the compound having two tert-butyl-substituted phenyl groups represented by the following Formula.

[Chemical Formula 3]

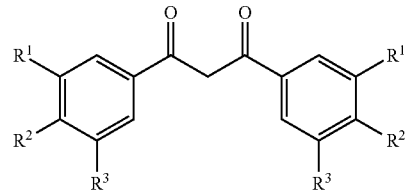

In the above Formula, $R^1$, $R^2$, and $R^3$ are each tert-butyl group or hydrogen atom. One phenyl group has at least one tert-butyl group, preferably two or more tert-butyl groups. The two tert-butyl groups may bond each other to thereby form a saturated hydrocarbon ring.

The structure of the particularly preferable β-diketone ligand is shown below. In the following Formula, t-Bu represents tert-butyl group.

[Chemical Formula 4]

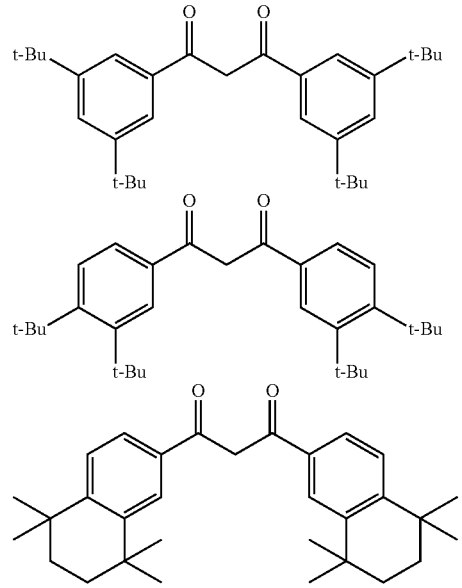

Next, the C—N ligand will be explained. A general formula of the C—N ligand applied to the present invention is represented by the following Formula.

[Chemical Formula 5]

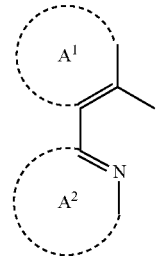

In the above C—N ligand, the upper-side atomic group $A^1$ is the unsaturated hydrocarbon ring, and is preferably a 6-membered ring. The $A^1$ is preferably a single heterocyclic ring or a single benzene ring, and the heteroatom in the heterocyclic ring is preferably nitrogen. Further, $A^1$ may have any substituent in the side chain, and the substituent is preferably fluorine atom (F), trifluoro (—$CF_3$) group, or cyano (—CN) group.

Specifically, as the atomic group $A^1$, any one shown in the following Formulae is preferable. In the following Formulae, the bonding site of $A^1$ to $A^2$ is designated by a downward dotted line.

[Chemical Formula 6]

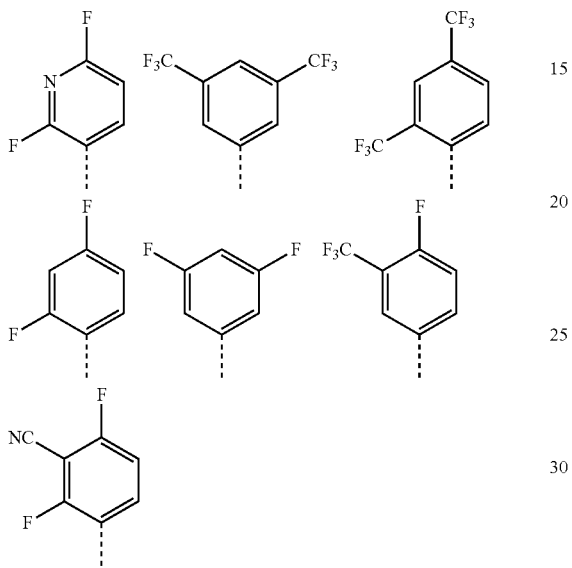

The atomic group $A^2$ of the C—N ligand in the lower side is preferably a single heterocyclic ring, and the hetero atom is preferably nitrogen. Further, the $A^2$ may have any substituent in the side chain, and the preferred substituent includes fluorine atom (F), trifluoro (—$CF_3$) group, an alkyl group (—R, having 1 or more and 10 or less, preferably 1 or more and 4 or less carbons), an alkoxy group (—OR, having 1 or more and 4 or less carbons). Note that the $A^2$ is also an unsaturated hydrocarbon similar to the $A^1$, and is preferably a 6-membered ring.

Specifically, as the atomic group $A^2$, any one shown in the following Formulae is preferable. In the following Formula, the bonding site of $A^2$ to $A^1$ is designated by a downward dotted line.

[Chemical Formula 7]

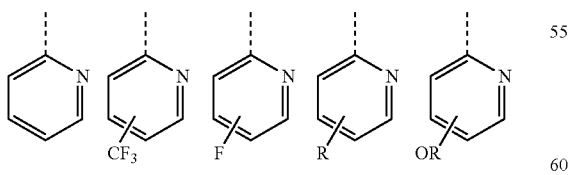

In the aforementioned Formula, R is an alkyl group having 1 or more and 10 or less carbons.

The C—N ligand having the aforementioned atomic groups $A^1$ and $A^2$ includes the following compounds, for example.

[Chemical Formula 8]

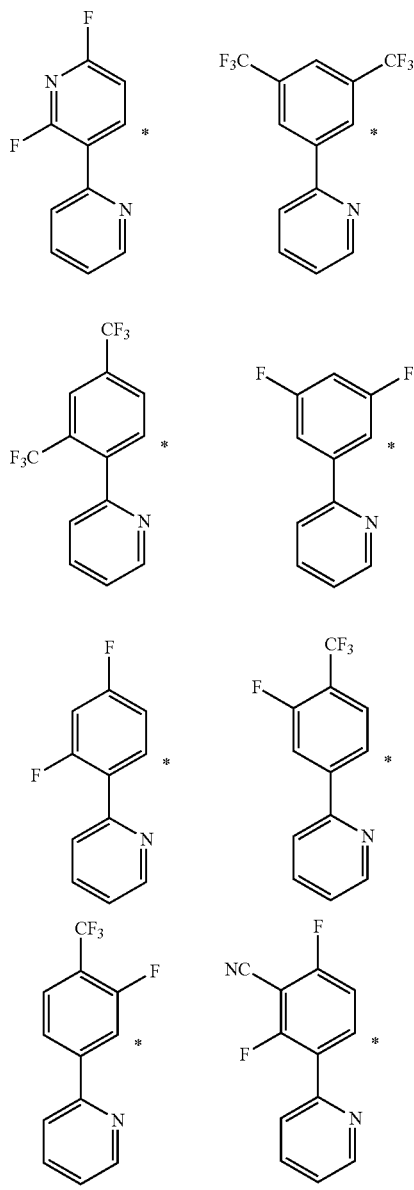

In the Formula, the symbol * shows the carbon which bonds to iridium.

[Chemical Formula 9]

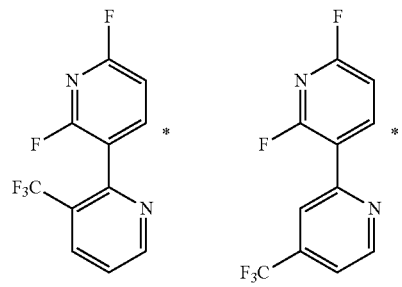

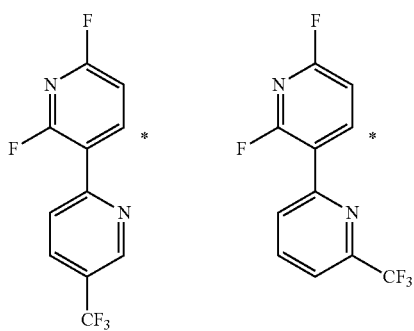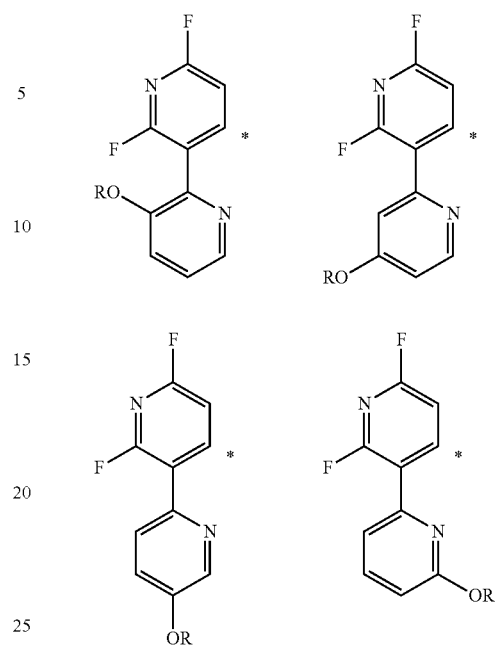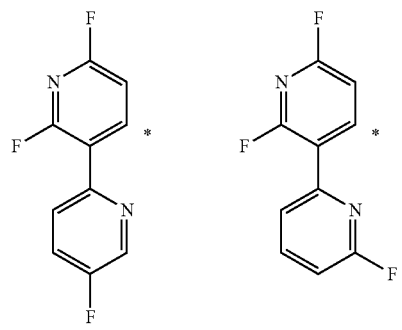
In the Formula, the symbol * shows the carbon which bonds to iridium.
[Chemical Formula 10]
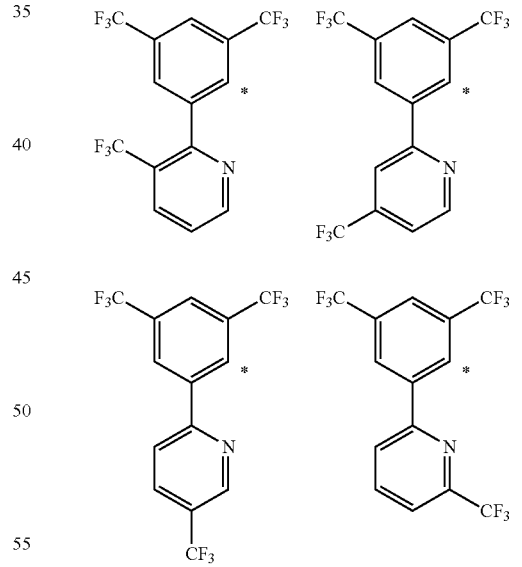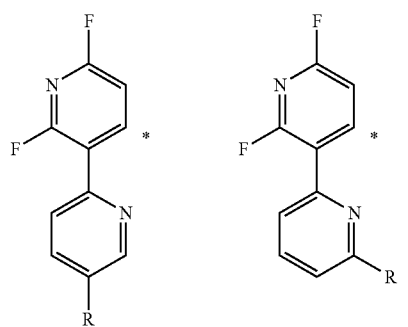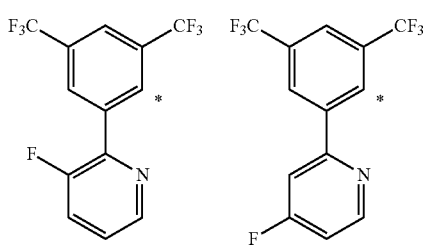

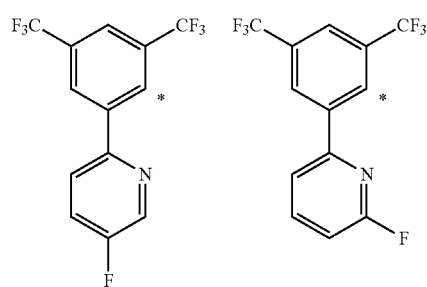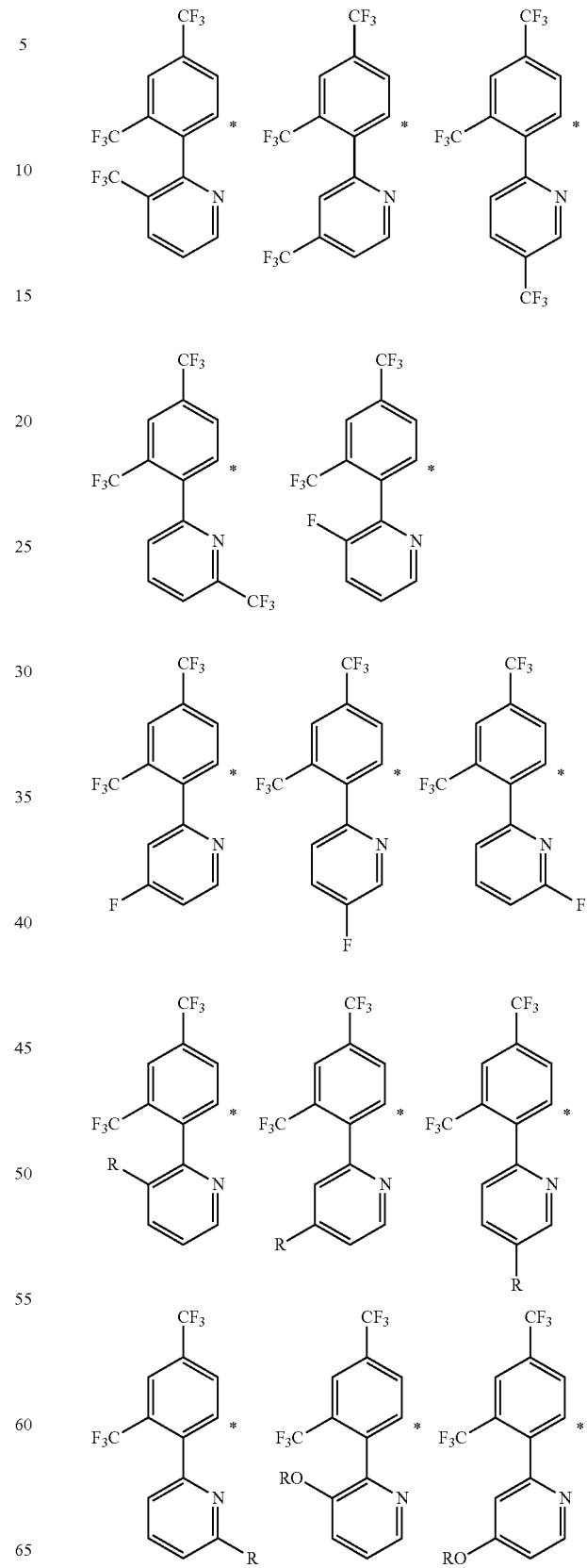
[Chemical Formula 11]
In the Formula, the symbol * shows the carbon which bonds to iridium.

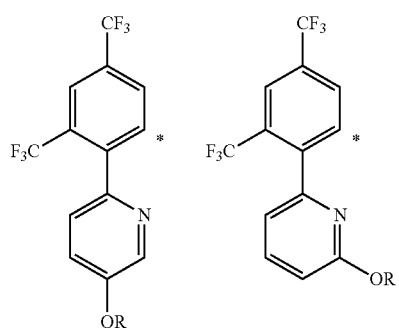
In the Formula, the symbol * shows the carbon which bonds to iridium.
[Chemical Formula 12]
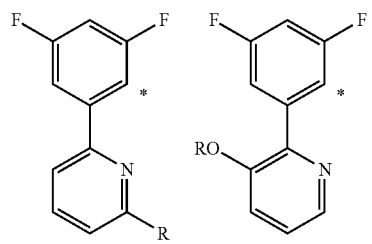
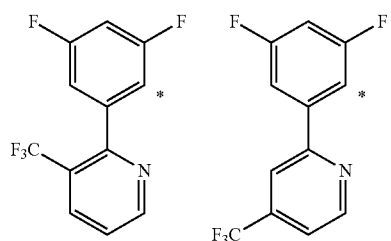
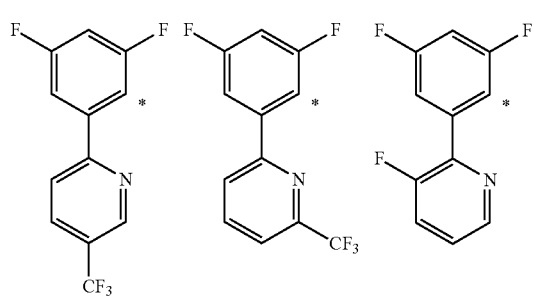
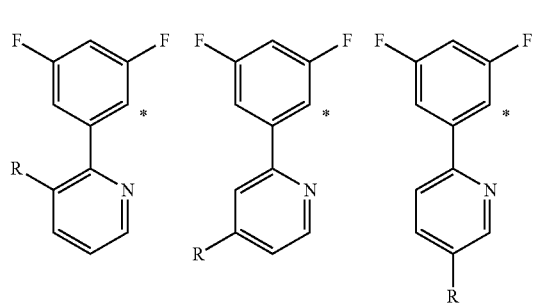
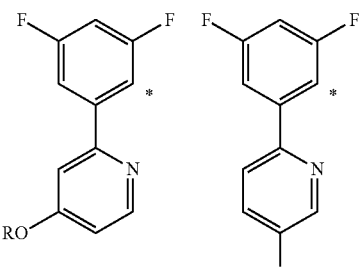
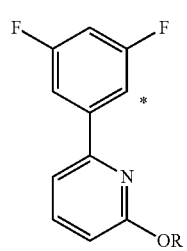
In the Formula, the symbol * shows the carbon which bonds to iridium.
[Chemical Formula 13]
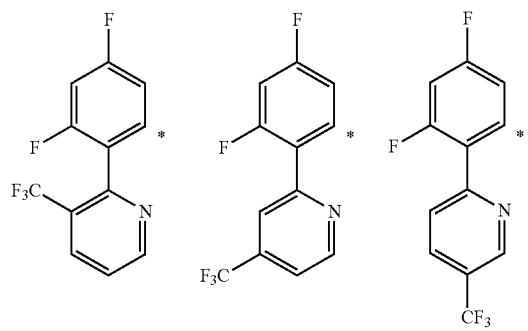
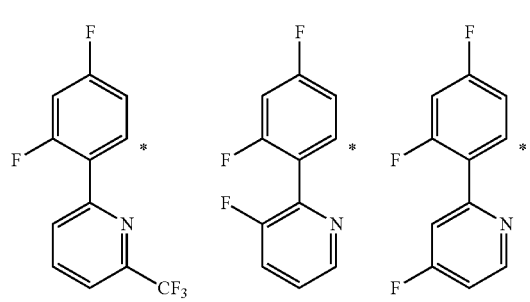

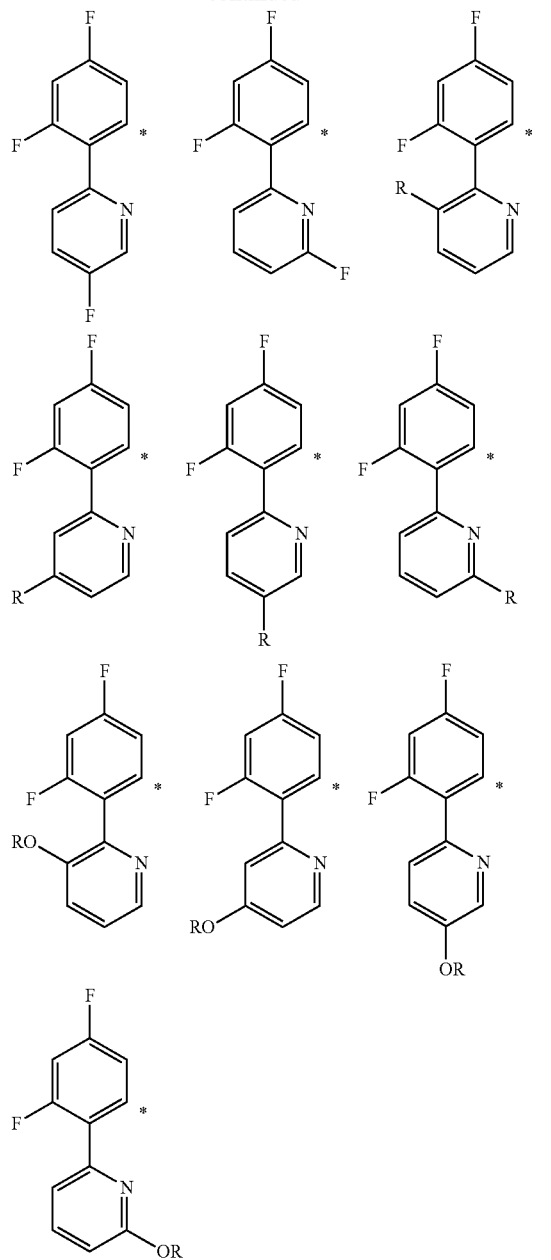
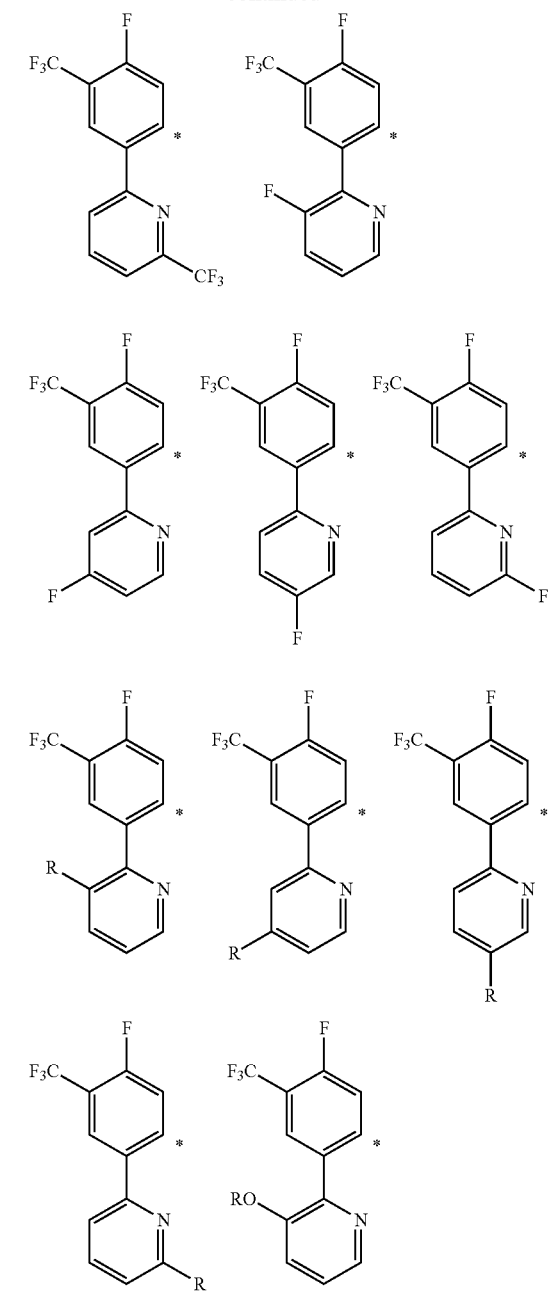
In the Formula, the symbol * shows the carbon which bonds to iridium.

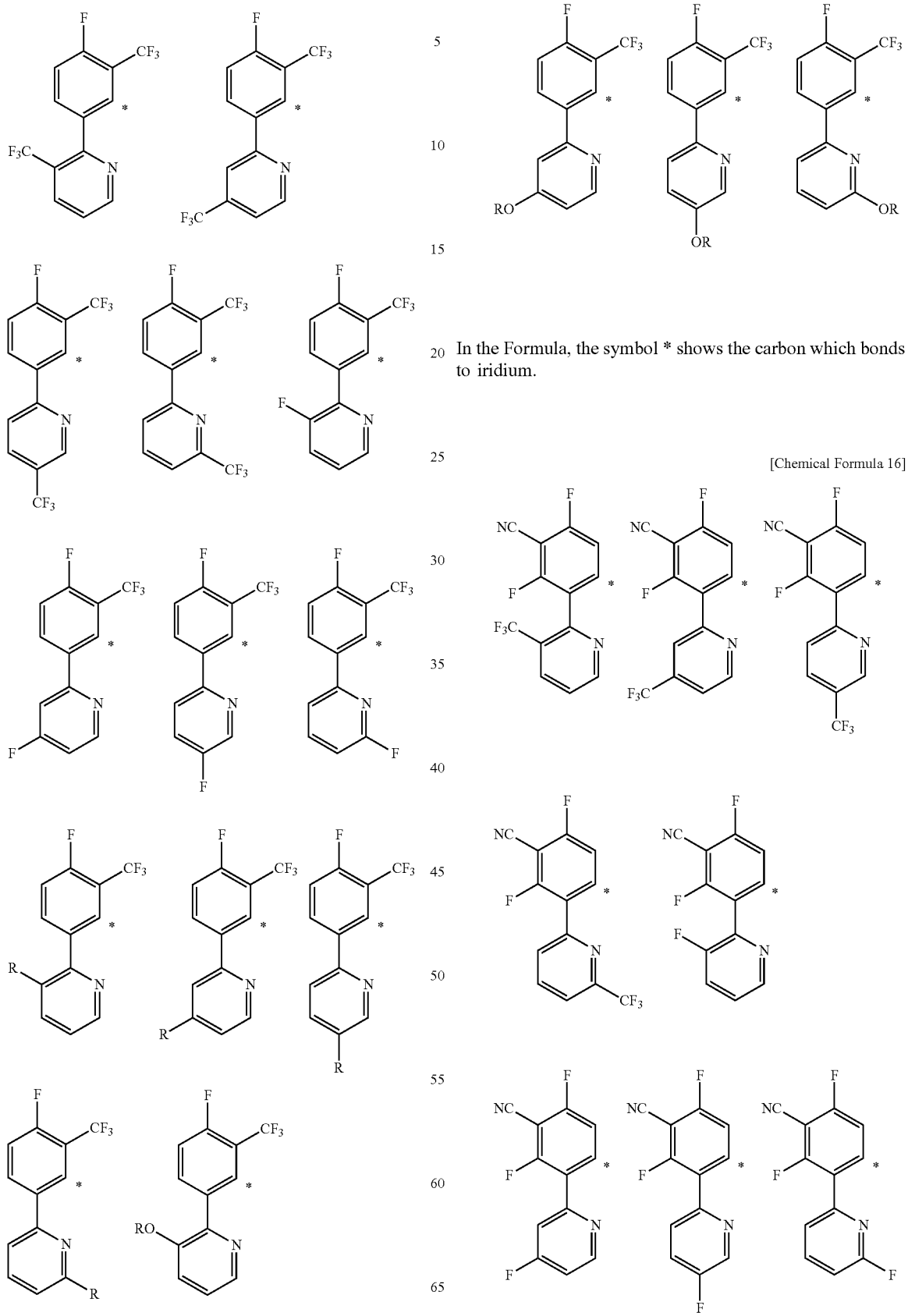
In the Formula, the symbol * shows the carbon which bonds to iridium.

-continued

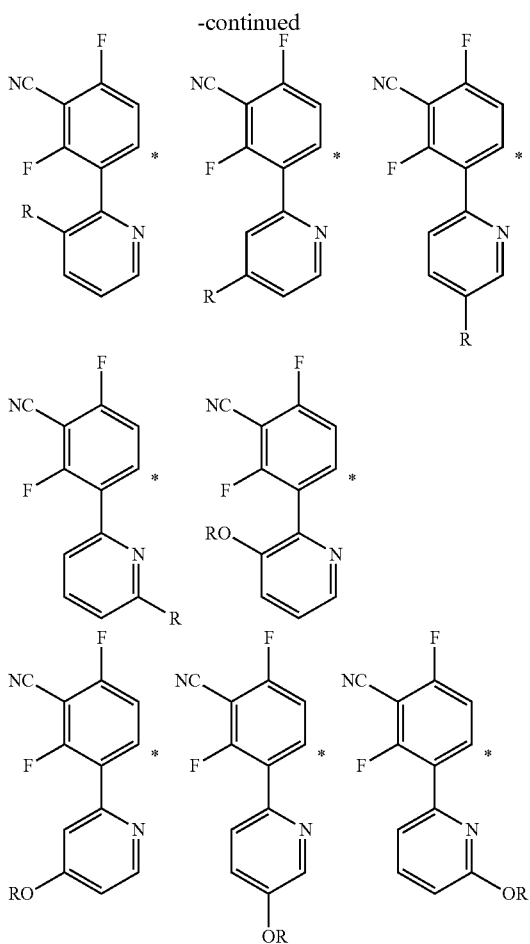

In the Formula, the symbol * shows the carbon which bonds to iridium.

The organoiridium complex of the present invention mentioned above has high light emission efficiency, and when 0.05 mmol/g doping is performed in a polymer thin film, the internal quantum efficiency $\varphi_{PL}$ is 0.45 or more. Therefore, the organoiridium complex is suitable for implementation to the organic electroluminescent element as the emission layer.

Furthermore, the organoiridium complex of the present invention tends to show a particularly high photoluminescence quantum yield in the polymer thin film in the range of the emission light color of yellow to green. Specifically, a light emission wavelength ($\lambda_{PL}$) in the polymer thin film is suitably 510 nm or more and 580 nm or less, particularly suitably 510 nm or more and 550 nm or less.

The organoiridium complex can be synthesized by reacting an iridium salt and a nitrogen-containing compound that constitutes the C—N ligand with each other by heating to thereby give a precursor, and then by reacting the precursor and a β-diketone compound with each other by heating. Alternatively, the organoiridium complex can also be synthesized by reacting a metal salt with a β-diketone compound, and then by reacting the resultant compound with a nitrogen-containing compound. The heating reaction for obtaining the precursor is preferably carried out at 80° C. or more and 130° C. or less for 12 hours or more and 24 hours or less, and the heating reaction with the β-diketone is preferably carried out at 60° C. or more and 130° C. or less for 0.5 hour or more and 12 hours or less. The reactions are preferably carried out in the presence of a solvent. The preferred iridium salt to be used in the aforementioned synthetic reaction is a chloride (IrCl$_3$). Furthermore, a hydrate of the chloride can be used as the form of use.

When the organoiridium complex mentioned above is applied to the organic EL element, the emission layer can be formed by a method such as spin coating method or vacuum deposition method. An element can be easily and inexpensively formed in the spin coating method.

Advantageous Effects of Invention

The organoiridium complex of the present invention is suitable as a emitting material of the organic EL element because of high photoluminescence quantum yield in the polymer thin film.

DESCRIPTION OF EMBODIMENTS

Figure 1:
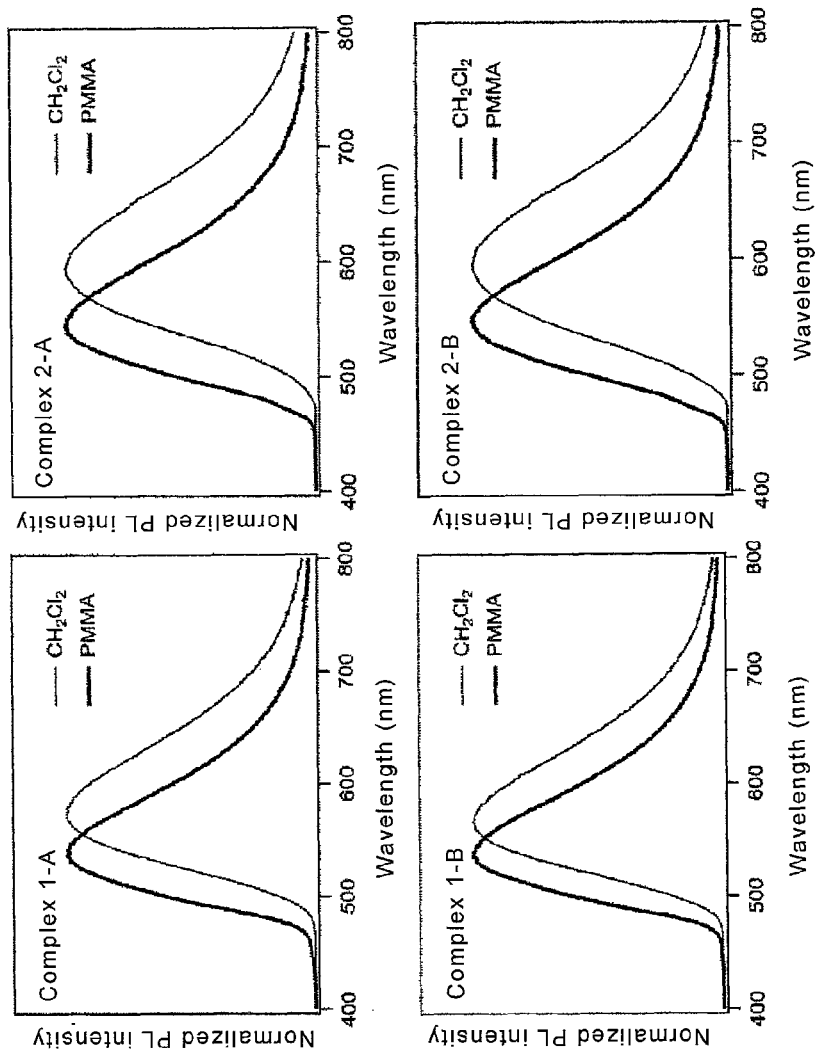
FIG. 1 shows the results of the light emission property of the organoiridium complex according to the embodiment.

Hereinafter, there will be explained the preferred embodiments according to the present invention.

The following organoiridium complexes having the respective ligands were synthesized, and the emission spectrum of the obtained complexes was measured and the photoluminescence quantum yield was evaluated. X is a β-diketone ligand in the conventional example. Each iridium complex was synthesized by reacting an iridium salt and a nitrogen-containing compound to obtain a precursor, and then reacting the precursor and the β-diketone compound.

[Chemical Formula 17]

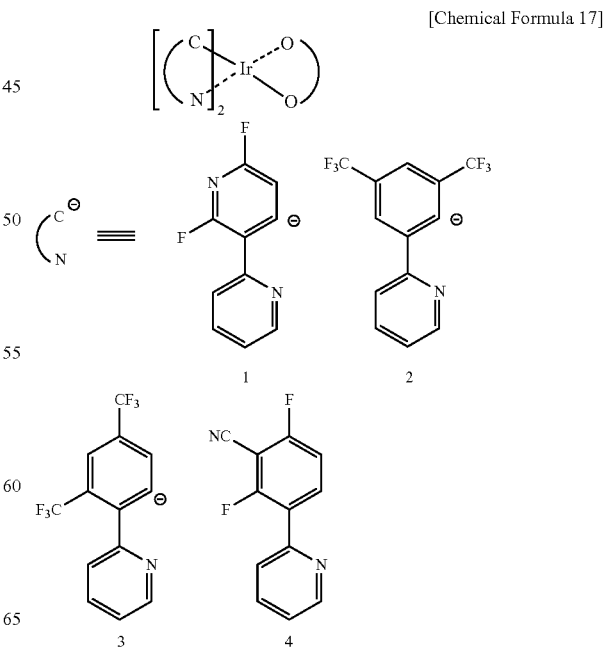

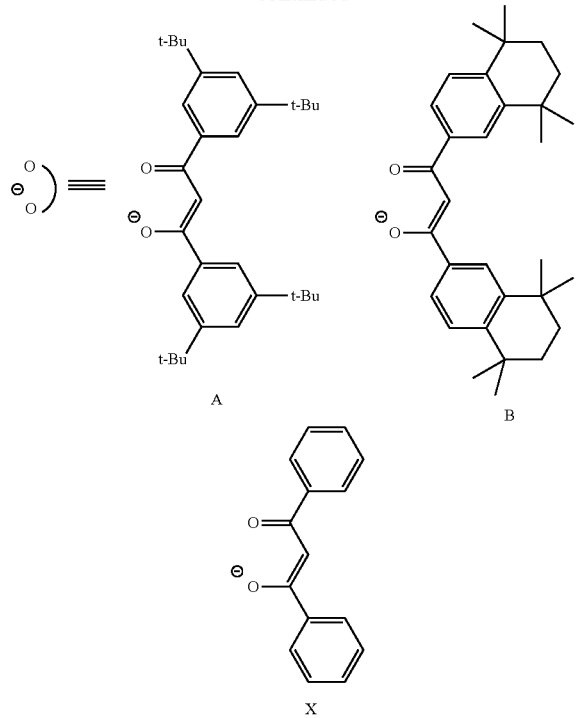

First, summary of the synthetic method of each of the aforementioned iridium complexes is explained. Firstly, each of the β-diketone compounds and each of the C—N ligands (1: 2',6'-difluoro-2,3'-bipyridine), (2: 2-(3,5-bis(trifluoromethyl)phenyl)pyridine), (3: 2-(2,4-bis(trifluoromethyl)phenyl)pyridine) was synthesized. Then, each of the C—N ligands was reacted respectively with iridium chloride to synthesize precursors (1), (2) and (3). Each iridium complex described above was obtained by reacting each precursor with the β-diketone compound.

All of the starting materials, the reagents and solvents used for the synthesis were those having commercially available reagent grades without purification. Also with respect to dibenzoylmethane (β-diketone (X)), the commercially available compound was used as it was for the complex synthesis. The commercially available dehydrated THF was used as the dry THF as it was. In addition, a spherical silica gel (neutral) manufactured by KANTO CHEMICAL CO., INC. was used as a filler to be used for a column chromatography.

A proton nuclear magnetic resonance ($^1$H NMR) spectrum and a mass analysis (mass (MS) spectrum) were used for identification of the synthesized complexes. Jeol JNM-ECX400 spectrophotometer (400 MHz) or Jeol JNM-ECS400 spectrophotometer (400 MHz) was used for measurement of the $^1$H NMR spectrum. The MS spectrum was measured by subjecting a sample ionized by an electro-spray ionization method (ESI method), or a matrix-assisted laser desorption ionization method (MALDI method) to the time-of-flight (TOF) type mass spectrometry (ESI-TOF-MS and MALDI-TOF-MS spectrum). Note that, in the MALDI-TOF-MS spectrum, α-cyano-4-hydroxycinnamic acid (CHCA) was used as a matrix. For the ESI-TOF-MS measurement, Jeol JML-T100LP mass spectrometry analyzer was used, and for the MALDI-TOF-MS measurement, Shimadzu-Kratos AXIMA-CFR PLUS TOF Mass mass spectrometry analyzer was used. Elemental analysis was performed by J-Science MICRO CORDER JM10 analysis machine by using acetanilide as a standard substance.

Synthesis of β-Diketone Compound (A)

After methyl 3,5-di(tert-butyl)benzoate and 3',5'-di(tert-butyl)acetophenone were synthesized from 3,5-di(tert-butyl) benzoic acid, the β-diketone compound (A) was obtained by the synthetic reaction using these two compounds.

Synthesis of methyl 3,5-di(tert-butyl)benzoate

A concentrated sulfuric acid (0.9 mL) was dropped onto a mixture of 3,5-di(tert-butyl)benzoic acid (3.00 g, 12.8 mmol) and methanol (9 mL) under a nitrogen atmosphere at 0° C., followed by heating and refluxing the resulting substance for 1 hour with stirring. After being allowed to cool, chloroform (100 mL) was added, and further water (100 mL) was added, with the result that an organic layer was separated by shaking in a separating funnel. After repeating this procedure again, the separated organic layers were combined into one. After further washing the organic layer with a saturated aqueous sodium bicarbonate solution (50 mL) and a saturated saline (50 mL), the organic layer was then dried by addition of an appropriate amount of anhydrous magnesium sulfate. After removal of the magnesium sulfate by filtration, methyl 3,5-di(tert-butyl)benzoate was obtained by distilling the solvent with an evaporator, and by drying the residue in a desiccator under a reduced pressure. The obtained compound was a white solid, and a yield was 92% (2.92 g, 11.8 mmol). The properties ($^1$H NMR, TOF MS) of the compound thus synthesized were as follows.

$^1$H NMR (CDCl$_3$): δ1.35 (s, 18H), 3.91 (s, 3H), 7.62 (t, J=2.0 Hz, 1H), 7.89 (d, J=2.0 Hz, 2H)

MALDI-TOF MS: m/z 249 ([M+H]$^+$)

[Chemical Formula 18]

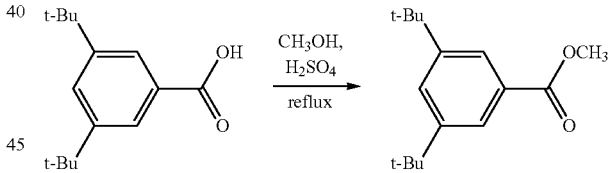

Synthesis of 3',5'-di(tert-butyl)acetophenone 3,5'-di(tert-t-butyl)benzoic acid (3.00 g, 12.8 mmol) was added to a dry tetrahydrofuran (120 mL), and was cooled to 0° C. or less with stirring under a nitrogen atmosphere. 3.0 M methyl lithium solution in diethoxymethane (15 mL) was dropped onto the mixture, and after raising the temperature to a room temperature, was stirred for 2 hours. After adding a 6 M hydrochloric acid to the reaction mixture to be acidic, extraction with chloroform (100 mL×2) was carried out. The obtained organic layers were combined into one, and after washing with water (50 mL×2), a saturated aqueous sodium bicarbonate solution (50 mL) and a saturated saline (50 mL), an appropriate amount of anhydrous magnesium sulfate was added for drying. After removal of the magnesium sulfate by filtration, 3',5'-di(tert-butyl)acetophenone was obtained by distilling the solvent with an evaporator, and by purifying the residue with a silica gel column chromatography (development solvent; chloroform). The obtained compound was a colorless liquid, and a yield was 75% (2.23 g, 9.60 mmol). The properties of the thus obtained compound were as follows.

$^1$H NMR (CDCl$_3$) δ1.37 (s, 18H), 2.60 (s, 3H), 7.64 (t, J=1.6 Hz, 1H), 7.80 (d, J=1.6 Hz, 2H)

MALDI-TOF MS: m/z 232 (M$^+$)

[Chemical Formula 19]

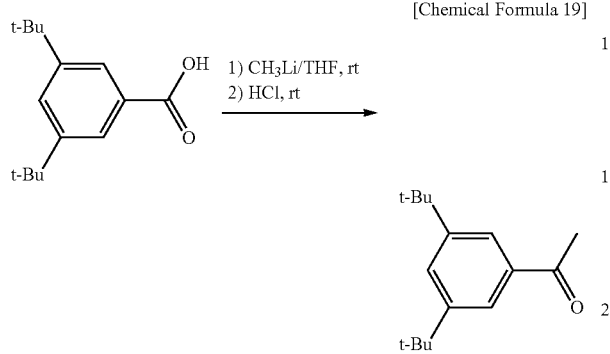

Synthesis of β-Diketone Compound (A)

Methyl 3,5-di(tert-butyl)bezoate (2.92 g, 11.8 mmol) and sodium hydride (60% oil dispersion; 1.27 g, 31.8 mmol) were added to a dry THF (23 mL), and were stirred at a room temperature under a nitrogen atmosphere. Then, a solution obtained by dissolving the 3',5'-di(tert-butyl)acetophenone (2.23 g, 9.60 mmol) in a dry THF (23 mL) was dropped onto the resultant substance for 30 minutes. Subsequently, the obtained reaction mixture was stirred for 24 hours at 60° C. After being allowed to cool, and after adding a 1 M hydrochloric acid to be acidic, extraction with chloroform (100 mL×2) was carried out. The obtained organic layers were combined into one, and after washing with water (50 mL×2), a saturated aqueous sodium bicarbonate solution (50 mL) and a saturated saline (50 mL), an appropriate amount of anhydrous magnesium sulfate was added for drying. After removal of the magnesium sulfate by filtration, 1,3-bis(3,5-di-(tert-butyl)phenyl) propane-1,3-dion(β-diketone A) was obtained by distilling the solvent with an evaporator, and by purifying the residue with a silica gel column chromatography (development solvent; chloroform). The obtained compound was an amber syrup substance, and a yield was 49% (2.12 g, 4.73 mmol). The properties of the thus obtained compound were as follows.

$^1$H NMR (CDCl$_3$) δ1.38 (s, 36H), 6.78 (s, 1H), 7.63 (t, J=2.0 Hz, 2H), 7.78 (d, J=2.0 Hz, 4H), 16.9 (brs, 1H)

MALDI-TOF MS: m/z 449 ([M+H]$^+$)

[Chemical Formula 20]

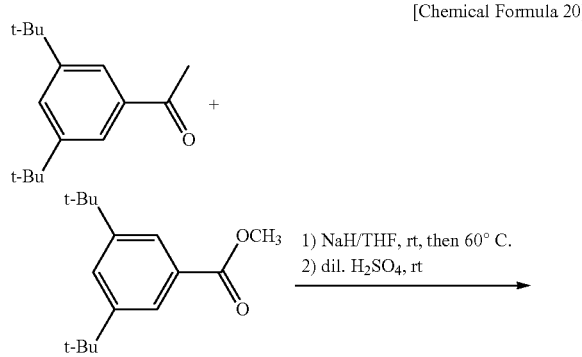

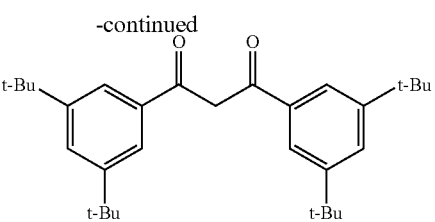

Synthesis of β-Diketone Compound (B)

The β-diketone compound (B) was obtained by the synthetic reaction of 1,2,3,4-tetrahydro-1,1,4,4-tetramethylnaphthalene and malonyl chloride.

Synthesis of β-Diketone Compound (B)

1,2,3,4-tetrahydro-1,1,4,4-tetramethylnaphthalene (5.00 g, 26.6 mmol), malonyl chloride (1.35 g, 9.58 mmol) and aluminum chloride (5.51 g, 41.3 mmol) were added to carbon disulfide (27 mL), and were heated and stirred at 50° C. Next, a cooled 2 mol/L hydrochloric acid (27 mL) was added, and after transferring to a separating funnel, extraction was carried out with chloroform. The organic layer was further washed with water, and after distilling the solvent with an evaporator, a concentrated hydrochloric acid (3.5 mL) and chloroform (35 mL) were added, and were then heated and refluxed for 9 hours. After being allowed to cool, the mixture was transferred to a separatory funnel, and was washed with water and a saturated saline. The solvent was distilled off with a rotary evaporator after drying the organic layer by using an anhydrous magnesium sulfate. The β-diketone (B) was obtained in a yield of 39% (1.66 g, 3.74 mmol) by purifying the residue with a silica gel column chromatography (development solvent; ethyl acetate:hexane=1:2 (v/v)). The properties of the thus obtained compound were as follows.

$^1$H NMR (CDCl$_3$): δ1.30 (s, 12H), 1.34 (s, 12H), 1.71 (m, 8H), 6.76 (s, 1H), 7.40 (d, J=8.0 Hz, 2H), 7.68 (dd, J=8.0 and 2.0 Hz, 2H), 7.94 (d, J=2.0 Hz, 2H), 16.96 (brs, 1H)

MALDI-TOF MS: m/z 445 ([M+H]$^+$)

[Chemical Formula 21]

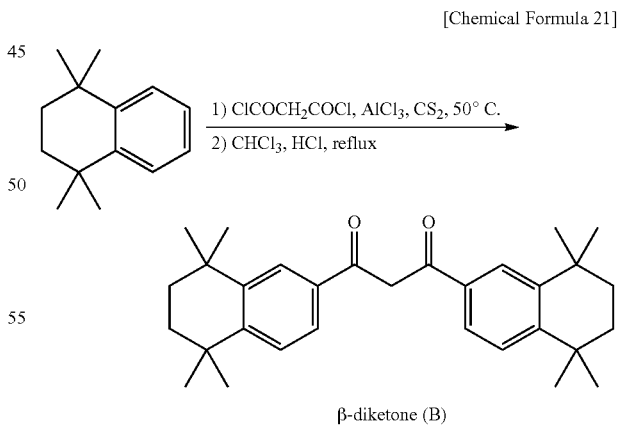

β-diketone (B)

Next, the C—N ligands (1) to (4) were synthesized according to the following manner.

Synthesis of C—N Ligand (1)

In accordance with the following formula, a C—N ligand (1) was obtained by reacting 2,6-difluoropyridineboronic acid with 2-bromopyridine. A mixture of 2,6-difluoropyridineboronic acid (2.08 g, 13.1 mmol), 2-bromopyridine (1.34 g, 8.48 mmol), THF (65 mL), water (26 mL), K₂CO₃ (1.51 g, 10.9 mmol) and Pd(PPh₃)₄ (0.67 g, 0.580 mmol) was heated and refluxed for 16 hours under a nitrogen atmosphere. After being allowed to cool, the mixture was concentrated to approximately ⅓ in solution volume by a rotary evaporator, and then the obtained mixture was transferred to a separating funnel. After diluting with an appropriate amount of chloroform, the mixture was washed with water and a saturated saline, and the organic layer was dried on anhydrous magnesium sulfate. After removal of the magnesium sulfate by filtration, the solvent of the filtrate was distilled off with a rotary evaporator. The C—N ligand (1) was obtained in a yield of 93% (1.51 g, 7.86 mmol) by purifying the residue with a silica gel chromatography (development solvent; ethyl acetate:hexane=1:3 (v/v)). The ¹H NMR property of the thus synthesized compound was as follows.

¹H NMR (CDCl₃): δ6.93 (dd, J=3.2, and 8.4 Hz, 1H), 7.20-7.32 (m, 1H), 7.68-7.86 (m, 2H), 8.56-8.73 (m, 2H)

[Chemcial Formula 22]

Synthesis of C—N Ligand (2)

In accordance with the following formula, a C—N ligand (2) was obtained by reacting 3,5-bis(trifluoromethyl)phenylboronic acid with 2-iodopyridine. A mixture of 3,5-bis(trifluoromethyl)phenylboronic acid (2.00 g, 7.75 mmol), 2-iodopyridine (1.17 g, 5.71 mmol), THF (30 mL), water (10 mL), K₂CO₃ (4.50 g, 32.6 mmol) and Pd(PPh₃)₄ (0.261 g, 0.226 mmol) was heated and refluxed for 48 hours under a nitrogen atmosphere. After being allowed to cool, the mixture was concentrated to approximately ⅓ in solution volume by a rotary evaporator, and then the obtained mixture was transferred to a separating funnel. After diluting with an appropriate amount of chloroform, the mixture was washed with water and a saturated saline, and the organic layer was dried on anhydrous magnesium sulfate. After removal of the magnesium sulfate by filtration, the solvent of the filtrate was distilled off with a rotary evaporator. The C—N ligand (2) was obtained in a yield of 51% (0.850 g, 2.92 mmol) by purifying the residue with a silica gel chromatography (development solvent; chloroform). The ¹H NMR property of the thus synthesized compound was as follows.

¹H NMR (CDCl₃): δ7.34-7.38 (m, 1H), 7.81-7.87 (m, 2H), 7.92 (s, 1H), 8.49 (s, 2H), 8.76 (dt, J=2.2 and 5.0 Hz, 1H)

[Chemical Formula 23]

Synthesis of C—N Ligand (3)

In accordance with the following formula, a C—N ligand (3) was obtained by reacting 2,4-bis(trifluoromethyl)phenylboronic acid with 2-iodopyridine. A mixture of 2,4-bis(trifluoromethyl)phenylboronic acid (2.31 g, 8.96 mmol), 2-iodopyridine (1.16 g, 5.66 mmol), benzene (25 mL), ethanol (10 mL), K₂CO₃ (7.31 g, 52.9 mmol) and PdCl₂(PPh₃)₂ (0.383 g, 0.546 mmol) was heated and refluxed for 16 hours under a nitrogen atmosphere. After being allowed to cool, the reaction mixture was transferred to a separating funnel. After diluting with an appropriate amount of chloroform, the mixture was washed with water and a saturated saline, and the organic layer was dried on anhydrous magnesium sulfate. After removal of the magnesium sulfate by filtration, the solvent was distilled off with a rotary evaporator. The C—N ligand (3) was obtained in a yield of 59% (0.978 g, 3.36 mmol) by purifying the residue with a silica gel chromatography (development solvent; chloroform). The ¹H NMR property of the thus synthesized compound was as follows.

¹H NMR (CDCl₃): δ7.33 (ddd, J=7.8, 7.7 and 1.1 Hz, 1H), 7.42 (d, J=7.8 Hz, 1H), 7.64 (d, J=7.7 Hz, 1H), 7.76 (ddd, J=7.7, 7.7 and 1.9 Hz, 1H), 7.86 (d, J=8.3 Hz, 1H), 8.01 (s, 1H)

[Chemical Formula 24]

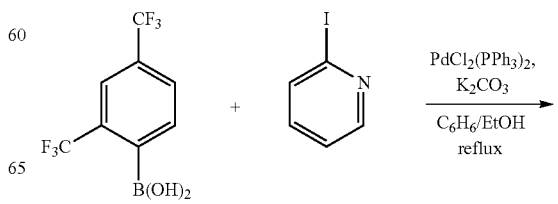

-continued

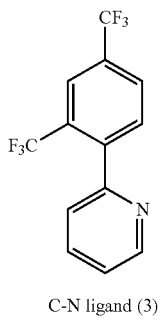

C-N ligand (3)

Synthesis of C—N Ligand (4)

In accordance with the following formula, a C—N ligand (4) was obtained by reacting 2,4-difluoro-3-cyanophenylboronic acid with 2-iodopyridine. A mixture of 2,4-difluoropyridineboronic acid (0.976 g, 5.34 mmol), 2-iodopyridine (0.733 g, 3.58 mmol), benzene (15 mL), ethanol (6 mL), water (15 mL), K$_2$CO$_3$ (4.56 g, 33.0 mmol) and Pd(PPh$_3$)$_2$Cl$_2$ (0.215 g, 0.306 mmol) was heated and refluxed for 18 hours under a nitrogen atmosphere. After being allowed to cool, the mixture was concentrated to approximately ⅓ in solution volume by a rotary evaporator, and then the obtained mixture was transferred to a separating funnel. After diluting with an appropriate amount of chloroform, the mixture was washed with water and a saturated saline, and the organic layer was dried on anhydrous magnesium sulfate. After removal of the magnesium sulfate by filtration, the solvent of the filtrate was distilled off with a rotary evaporator. The C—N ligand (4) was obtained in a yield of 80% (0.620 g, 2.87 mmol) by purifying the residue with a silica gel chromatography (development solvent; chloroform). The $^1$H NMR property of the thus synthesized compound was as follows.

$^1$H NMR (CDCl$_3$): δ7.18 (ddd, J=1.4, 7.8 and 9.2 Hz, 1H), 7.33 (ddd, J=1.4, 5.0 and 7.3 Hz, 1H), 7.76-7.84 (m, 2H), 7.86 (td, J=6.4 and 8.7 Hz, 1H), 8.72 (m, 1H)

[Chemical Formula 25]

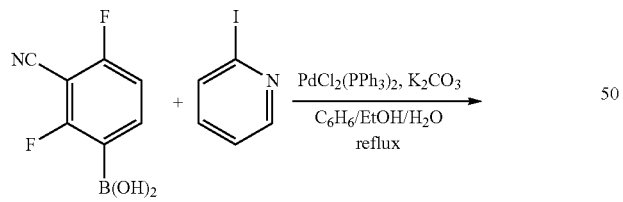

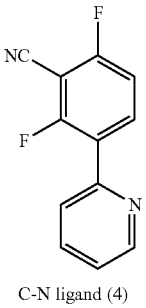

C-N ligand (4)

Precursor (1) to (3) were obtained by casing each of the thus synthesized C—N ligands and iridium chloride to react with each other.

Synthesis of Precursor (1)

In accordance with the following formula, a precursor (1) was obtained by casing the C—N ligand (1) and iridium chloride to react with each other. A mixture of 2',6'-difluoro-2,3'-bipyridine (0.500 g, 2.60 mmol), iridium chloride trihydrate (0.442 g, 1.25 mmol), water (17 mL) and 2-ethoxyethanol (48 mL) was stirred for 12 hours at 100° C. After being allowed to cool, the mixture was concentrated by a rotary evaporator, water (50 mL) was added to the mixture. The resulting precipitant was recovered by suction filtration, and then the precursor (1) was obtained in a yield of 73% (0.580 g, 0.475 mmol) by washing with an appropriate amount of methanol. The thus obtained compound was an insoluble solid. Without further purification, the compound was used for the following synthesis of an iridium complex.

[Chemical Formula 26]

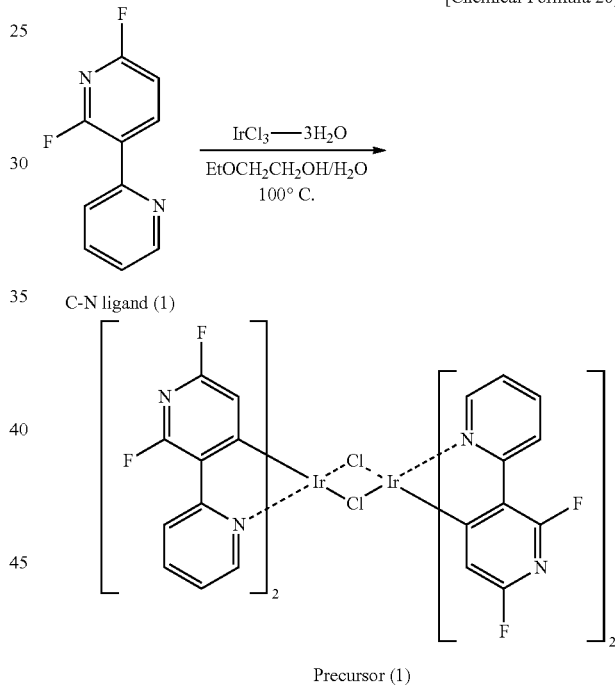

Synthesis of Precursor (2)

In accordance with the following formula, a precursor (2) was obtained by casing the C—N ligand (2) and iridium chloride to react with each other. A mixture of 2-(3,5-bis(trifluoromethyl)phenyl)pyridine (0.850 g, 2.92 mmol), iridium chloride trihydrate (0.430 g, 1.22 mmol), water (20 mL) and 2-ethoxyethanol (48 mL) was stirred for 12 hours at 100° C. After being allowed to cool, the mixture was concentrated by a rotary evaporator, water (50 mL) was added to the mixture. The resulting precipitant was recovered by suction filtration, and then the precursor (2) was obtained in a yield of 79% (0.930 g, 0.575 mmol) by washing with an appropriate amount of methanol. The thus obtained compound was an insoluble solid. Without further purification, the compound was used for the following synthesis of an iridium complex.

[Chemical Formula 27]

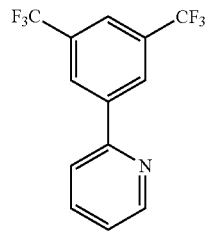

C-N ligand (2)

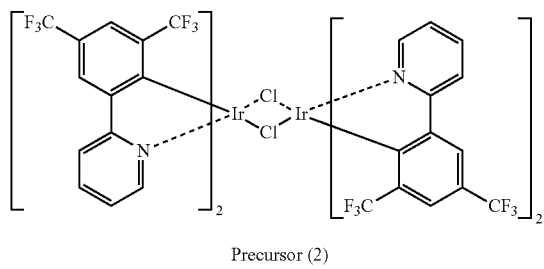

Precursor (2)

Synthesis of Precursor (3)

In accordance with the following formula, a precursor (3) was obtained by casing the C—N ligand (3) and iridium chloride to react with each other. A mixture of 2-(2,4-bis(trifluoromethyl)phenyl)pyridine (0.431 g, 1.48 mmol), iridium chloride trihydrate (0.264 g, 0.749 mmol), water (10 mL) and 2-ethoxyethanol (28 mL) was stirred for 12 hours at 100° C. After being allowed to cool, the mixture was concentrated by a rotary evaporator, water (30 mL) was added to the mixture. The resulting precipitant was recovered by suction filtration, and then the precursor (3) was obtained in a yield of 55% (0.329 g, 0.204 mmol) by washing with an appropriate amount of methanol. The thus obtained compound was an insoluble solid. Without further purification, the compound was used for the following synthesis of an iridium complex.

[Chemical Formula 28]

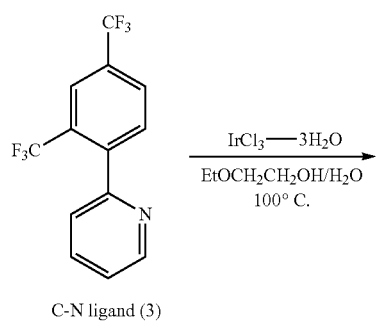

C-N ligand (3)

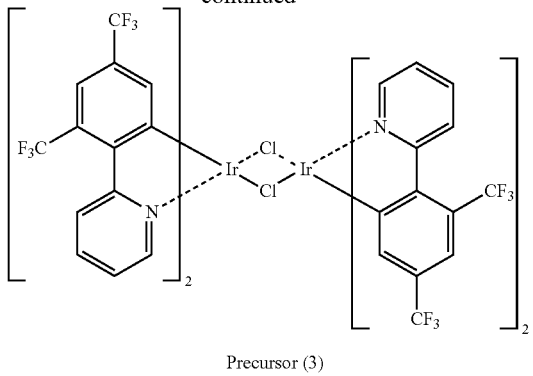

Precursor (3)

Synthesis of Precursor (4)

In accordance with the following formula, a precursor (4) was obtained by casing the C—N ligand (4) and iridium chloride to react with each other. A mixture of 2,6-difluoro-3-(pyridine-2-yl)benzonitrile (0.612 g, 2.83 mmol), iridium chloride trihydrate (0.492 g, 1.40 mmol), water (21 mL) and 2-ethoxyethanol (64 mL) was stirred for 25 hours at 100° C. After being allowed to cool, the mixture was concentrated by a rotary evaporator, water (50 mL) was added to the mixture. The resulting precipitant was recovered by suction filtration, and then the precursor (4) was obtained in a yield of 83% (0.762 g, 0.579 mmol) by washing with an appropriate amount of methanol. The thus obtained compound was an insoluble solid. Without further purification, the compound was used for the following synthesis of an iridium complex.

[Chemical Formula 29]

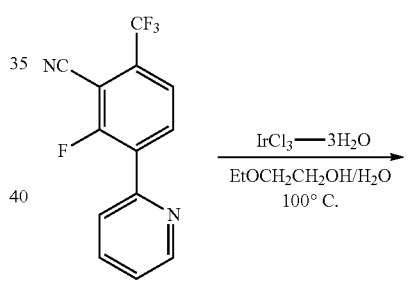

C-N ligand (4)

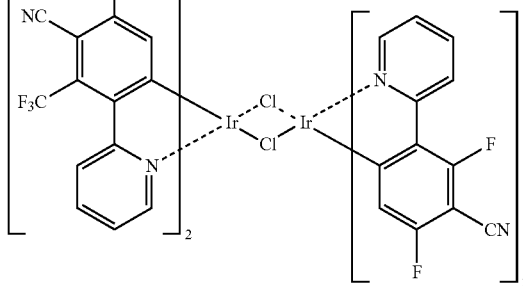

Precursor (4)

The thus synthesized precursors (1) to (4) and β-diketones (A), (B), and (X) were reacted with each other respectively to give respective iridium complexes.

Synthesis of Iridium Complex (1-A)

In accordance with the following formula, the iridium complex 1-A was obtained by reacting the precursor (1) and the β-diketone (A) with each other.

[Chemical Formula 30]

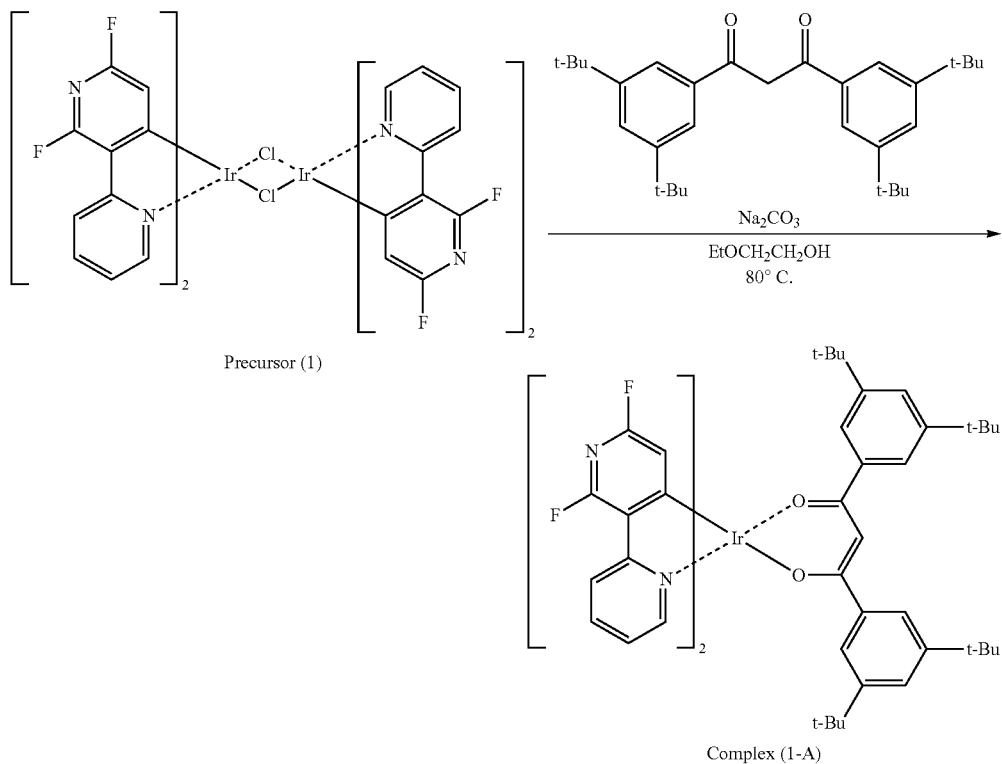

Precursor (1)

Complex (1-A)

Synthesis of Iridium Complex (1-A)

The precursor (1) (0.244 g, 0.200 mmol), 1,3-bis(3,5-di(tert-butyl)phenyl)propane-1,3-dione (β-diketone (A)), (0.131 g, 0.292 mmol) and sodium carbonate (1.90 g, 17.9 mmol) was added to 2-ethoxyethanol (50 mL), and the resulting mixture was stirred for 30 minutes at 80° C. under a nitrogen atmosphere. After being allowed to cool, the solvent was distilled off by a rotary evaporator, and then chloroform was added to the residue. The obtained mixed solution was washed with water and a saturated saline, and was then dried by adding an appropriate amount of anhydrous sodium sulfate. After removal of the sodium sulfate by filtration, the solvent of the filtrate was distilled off with a rotary evaporator. The iridium complex 1-A was obtained in a yield of 25% (73.5 mg, 0.0719 mmol) by purifying the obtained residue with a silica gel column chromatography (development solvent; methylene chloride), and by further performing recrystallization using acetonitrile. The properties of the thus synthesized compound were as follows.

$^1$H NMR (CDCl$_3$): δ1.26 (s, 36H), 5.81 (t, J=1.8 Hz, 2H), 6.58 (s, 1H), 7.19-7.22 (m, 2H), 7.53 (m, 6H), 7.85-7.89 (m, 2H), 8.29 (d, J=7.6 Hz, 2H), 8.57 (dd, J=0.80 and 6.0 Hz, 2H)

ESI-TOF MS: m/z 1045 ([M+Na]$^+$)

Anal. Calcd for C$_{51}$H$_{53}$F$_4$IrN$_4$O$_2$: C, 59.92; H, 5.23; 5.48. Found: C, 60.10; H, 5.03; 5.50.

Synthesis of Iridium Complex (1-B)

In accordance with the following formula, the iridium complex 1-B was obtained by reacting the precursor (1) and the β-diketone (B) with each other.

[Chemical Formula 31]

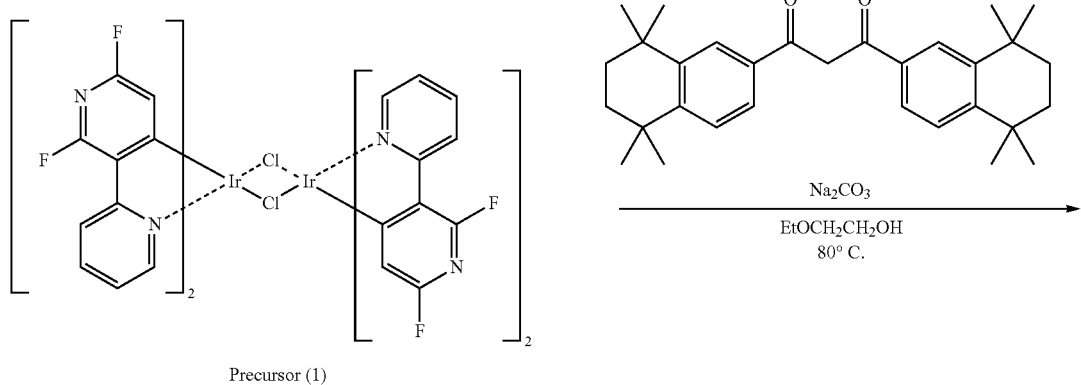

Precursor (1)

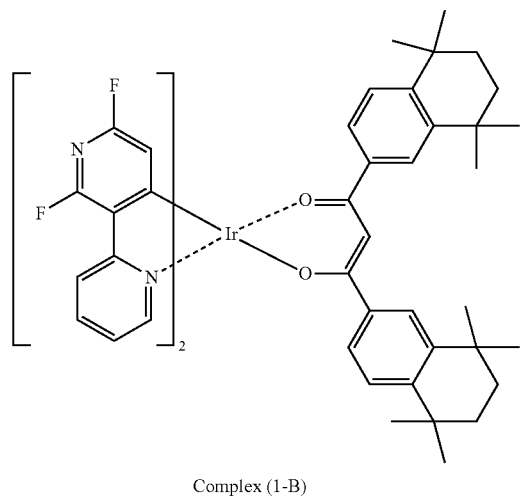

Complex (1-B)

Synthesis of Iridium Complex (1-B)

The precursor (1) (0.246 g, 0.201 mmol), β-diketone (B), (0.129 g, 0.290 mmol) and sodium carbonate (1.90 g, 17.9 mmol) was added to 2-ethoxyethanol (50 mL), and the resulting mixture was stirred for 30 minutes at 80° C. under a nitrogen atmosphere. After being allowed to cool, the solvent was distilled off by a rotary evaporator, and then chloroform was added to the residue. The obtained mixed solution was washed with water and a saturated saline, and was then dried by adding an appropriate amount of anhydrous sodium sulfate. After removal of the sodium sulfate by filtration, the solvent of the filtrate was distilled off with a rotary evaporator. The iridium complex 1-B was obtained in a yield of 25% (75.1 mg, 0.0738 mmol) by purifying the obtained residue with a silica gel column chromatography (development solvent; methylene chloride), and by further performing recrystallization using methanol. The properties of the thus synthesized compound were as follows.

$^1$H NMR (CDCl$_3$): δ1.23 (s, 12H), 1.25 (s, 12H), 1.66 (s, 8H), 5.76 (s, 2H), 6.58 (s, 1H), 7.17-7.21 (m, 2H), 7.29 (d, J=8.0 Hz, 2H), 7.49-7.52 (m, 2H), 7.71 (d, J=2.0 Hz, 2H), 7.83-7.87 (m, 2H), 8.27 (d, J=8.8 Hz, 2H), 8.53 (d, J=6.0 Hz, 2H)

ESI-TOF MS: m/z 1041 ([M+Na]$^+$)

Anal. Calcd for C$_{51}$H$_{49}$F$_4$IrN$_4$O$_2$: C, 60.16; H, 4.85; 5.50. Found: C, 60.12; H, 4.61; 5.45.

Synthesis of Iridium Complex (1-X)

In accordance with the following formula, the iridium complex 1-X was obtained by reacting the precursor (1) and the β-diketone (X) with each other.

[Chemical Formula 32]

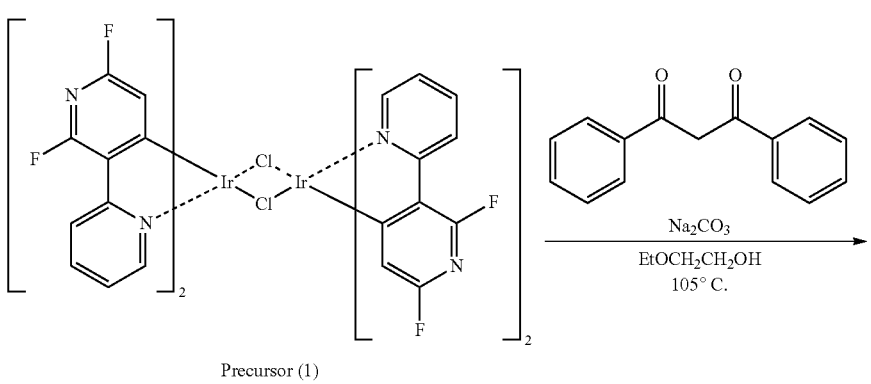

Precursor (1)

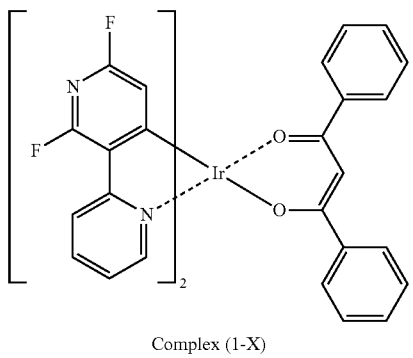

Complex (1-X)

Synthesis of Iridium Complex (1-X)

The precursor (1) (0.500 g, 0.410 mmol), β-diketone (X), (0.435 g, 1.94 mmol) and sodium carbonate (0.389 g, 3.67 mmol) was added to 2-ethoxyethanol (77 mL), and the resulting mixture was stirred for 2 hours at 105° C. under a nitrogen atmosphere. After being allowed to cool, the solvent was distilled off by a rotary evaporator, and then chloroform was added to the residue. The obtained mixed solution was washed with water and a saturated saline, and was then dried by adding an appropriate amount of anhydrous sodium sulfate. After removal of the sodium sulfate by filtration, the solvent of the filtrate was distilled off with a rotary evaporator. The iridium complex 1-X was obtained in a yield of 38% (250 mg, 0.313 mmol) by purifying the obtained residue with a silica gel column chromatography (development solvent; methylene chloride), and by further performing recrystallization using methanol. The properties of the thus synthesized compound were as follows.

$^1$H NMR (CDCl$_3$): δ5.75 (s, 2H), 6.66 (s, 1H), 7.23-7.25 (m, 2H), 7.35 (t, J=7.8 Hz, 4H), 7.45-7.47 (m, 2H), 7.77 (dd, J=1.2 and 7.8 Hz, 4H), 7.88 (t, J=7.8 Hz, 2H), 8.29 (d, J=8.0 Hz, 2H), 8.52 (d, J=6.0 Hz, 2H)

ESI-TOF MS: m/z 821 ([M+Na]$^+$)

Anal. Calcd for C$_{35}$H$_{21}$F$_4$IrN$_4$O$_2$: C, 52.69; H, 2.65; 7.02. Found: C, 52.92; H, 2.73; 7.01.

Synthesis of Iridium Complex (2-A)

In accordance with the following formula, the iridium complex 2-A was obtained by reacting the precursor (2) and the β-diketone (A) with each other.

[Chemical Formula 33]

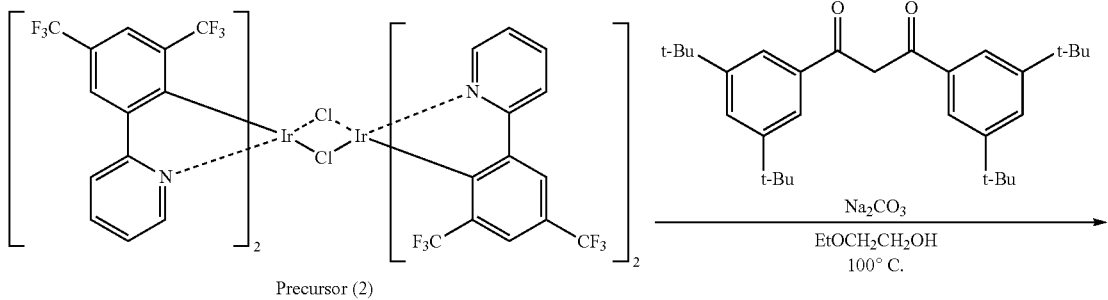

Precursor (2)

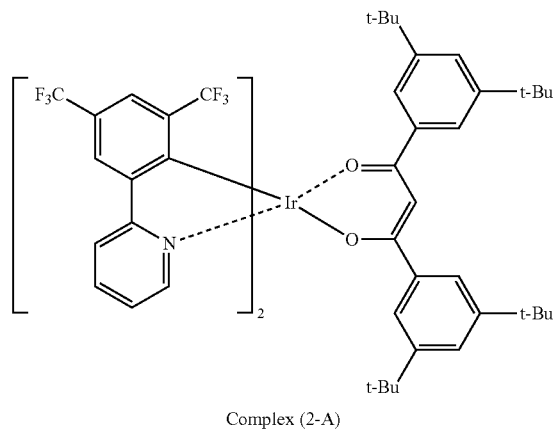

Complex (2-A)

Synthesis of Iridium Complex (2-A)

The precursor (2) (0.245 g, 0.152 mmol), 1,3-bis(3,5-di(tert-butyl)phenyl)propane-1,3-dione (β-diketone (A)), (0.129 g, 0.288 mmol) and sodium carbonate (1.90 g, 17.9 mmol) was added to 2-ethoxyethanol (50 mL), and the resulting mixture was stirred for 2 hours at 100° C. under a nitrogen atmosphere. After being allowed to cool, the solvent was distilled off by a rotary evaporator, and then chloroform was added to the residue. The obtained mixed solution was washed with water and a saturated saline, and was then dried by adding an appropriate amount of anhydrous sodium sulfate. After removal of the sodium sulfate by filtration, the solvent of the filtrate was distilled off with a rotary evaporator. The iridium complex 2-A was obtained in a yield of 5.8% (20.3 mg, 0.0166 mmol) by purifying the obtained residue with a silica gel column chromatography (development solvent; chloroform:hexane=1:1 (v/v)), and by further performing recrystallization using methanol. The properties of the thus synthesized compound were as follows.

$^1$H NMR (CDCl$_3$): δ1.24 (s, 36H), 6.34 (s, 1H), 6.94-6.97 (m, 2H), 7.30 (d, J=1.6 Hz, 4H), 7.48 (t, J=1.6 Hz, 2H), 7.55 (brs, 2H), 7.78 (dt, J=1.6 and 7.8 Hz, 2H), 8.05 (d, J=7.6 Hz, 2H), 8.16 (brs, 2H), 8.27 (d, J=6.0 Hz, 2H)

ESI-TOF MS: m/z 1243 ([M+Na]$^+$)

Anal. Calcd for C$_{57}$H$_{55}$F$_{12}$IrN$_2$O$_2$: C, 56.10; H, 4.54; 2.30. Found: C, 55.93; H, 4.49; 2.26.

Synthesis of Iridium Complex (2-B)

In accordance with the following formula, the iridium complex 2-B was obtained by reacting the precursor (2) and the β-diketone (B) with each other.

Synthesis of Iridium Complex (2-B)

The precursor (2) (0.154 g, 0.0953 mmol), β-diketone (B), (0.200 g, 0.450 mmol) and sodium carbonate (0.0900 g, 0.849 mop was added to 2-ethoxyethanol (18 mL), and the resulting mixture was stirred for 3 hours at 105° C. under a nitrogen atmosphere. After being allowed to cool, the solvent was distilled off by a rotary evaporator, and then chloroform was added to the residue. The obtained mixed solution was washed with water and a saturated saline, and was then dried by adding an appropriate amount of anhydrous sodium sulfate. After removal of the sodium sulfate by filtration, the solvent of the filtrate was distilled off with a rotary evaporator. The iridium complex 2-B was obtained in a yield of 39% (90.0 mg, 0.0740 mmol) by purifying the obtained residue with a silica gel column chromatography (development solvent; chloroform), and by further performing recrystallization using methanol. The properties of the thus synthesized compound were as follows.

$^1$H NMR (CDCl$_3$): δ1.16 (s, 12H), 1.23 (s, 12H), 1.64 (s, 8H), 6.32 (s, 1H), 6.91-6.95 (m, 2H), 7.22 (d, J=7.8 Hz, 2H), 7.30 (dd, J=2.0 and 7.8 Hz, 2H), 7.43 (d, J=2.0 Hz, 2H), 7.55 (s, 2H), 7.73-7.78 (m, 2H), 8.01 (d, J=8.0 Hz, 2H), 8.16 (s, 2H), 8.22 (d, J=6.0 Hz, 2H)

ESI-TOF MS: m/z 1239 ([M+Na]$^+$)

Anal. Calcd for C$_{57}$H$_{51}$F$_{12}$IrN$_2$O$_2$: C, 56.29; H, 4.23; 2.30. Found: C, 56.60; H, 4.40; 2.26.

Synthesis of Iridium Complex (2-X)

In accordance with the following formula, the iridium complex 2-X was obtained by reacting the precursor (2) and the β-diketone (X) with each other.

[Chemical Formula 34]

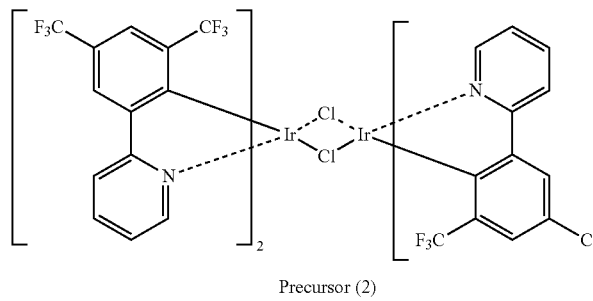

Precursor (2)

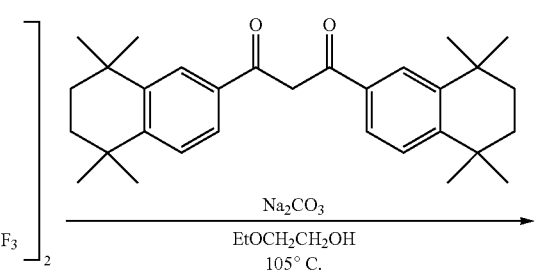

$$\xrightarrow[\text{EtOCH}_2\text{CH}_2\text{OH}]{\text{Na}_2\text{CO}_3} \quad 105°\text{ C.}$$

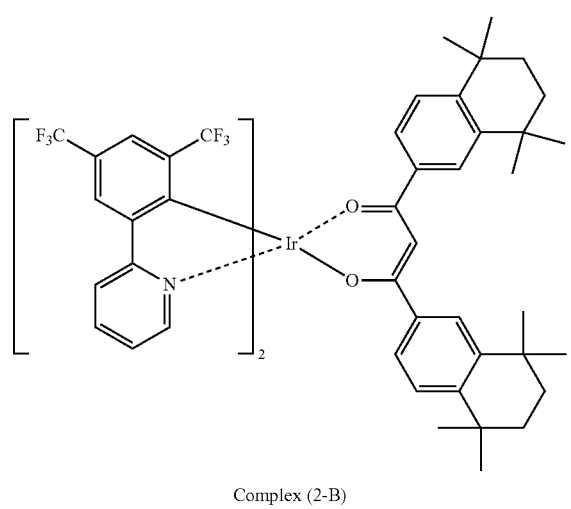

Complex (2-B)

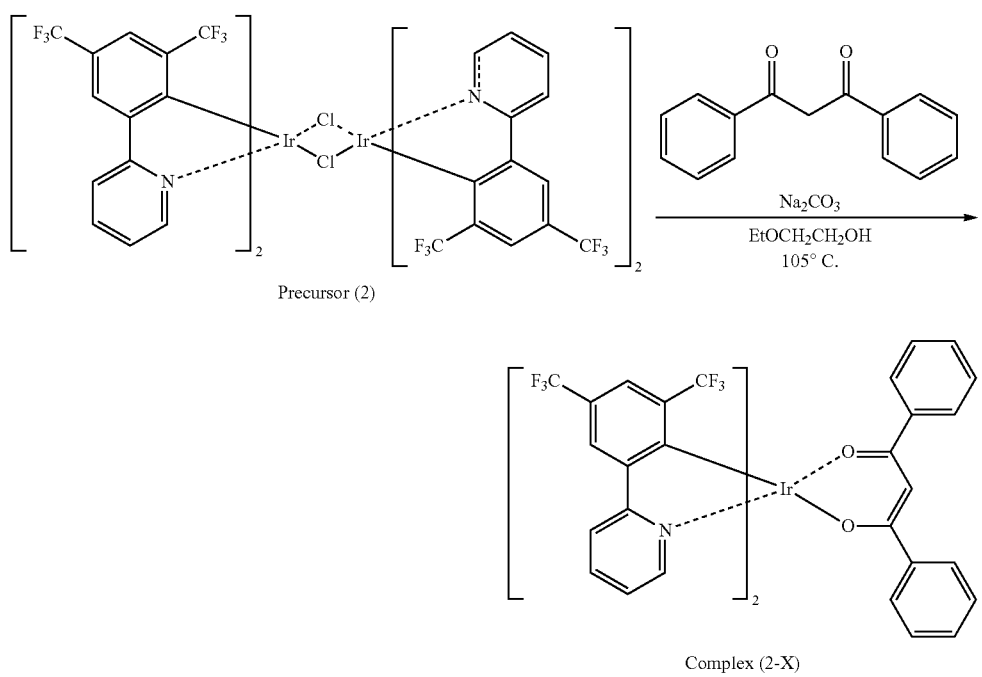

Precursor (2)

Complex (2-X)

Synthesis of Iridium Complex (2-X)

The precursor (2) (0.331 g, 0.205 mmol), β-diketone (X), (0.220 g, 0.981 mmol) and sodium carbonate (0.195 g, 1.84 mmol) was added to 2-ethoxyethanol (39 mL), and the resulting mixture was stirred for 3 hours at 105° C. under a nitrogen atmosphere. After being allowed to cool, the solvent was distilled off by a rotary evaporator, and then chloroform was added to the residue. The obtained mixed solution was washed with water and a saturated saline, and was then dried by adding an appropriate amount of anhydrous sodium sulfate. After removal of the sodium sulfate by filtration, the solvent of the filtrate was distilled off with a rotary evaporator. The iridium complex 2-X was obtained in a yield of 30% (120 mg, 0.121 mmol) by purifying the obtained residue with a silica gel column chromatography (development solvent; chloroform), and by further performing recrystallization using methanol. The properties of the thus synthesized compound were as follows.

$^1$H NMR (CDCl$_3$): δ6.43 (s, 1H), 6.94-6.98 (m, 2H), 7.29 (t, J=7.8 Hz, 4H), 7.41 (t, J=7.8 Hz, 2H), 7.55-7.57 (m, 6H), 7.74-7.78 (m, 2H), 8.00 (d, J=8.4 Hz, 2H), 8.13 (s, 2H), 8.21 (d, J=6.0 Hz, 2H)

ESI-TOF MS: m/z 1019 ([M+Na]$^+$)

Anal. Calcd for C$_{41}$H$_{23}$F$_{12}$IrN$_2$O$_2$·H$_2$O: C, 48.57; H, 2.49; 2.76. Found: C, 48.76; H, 2.60; 2.67.

Synthesis of Iridium Complex (3-A)

In accordance with the following formula, the iridium complex 3-A was obtained by reacting the precursor (3) and the β-diketone (A) with each other.

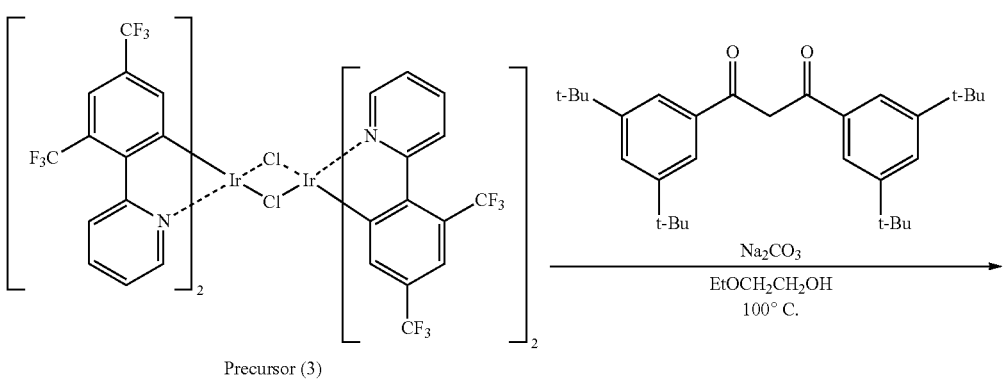

Precursor (3)

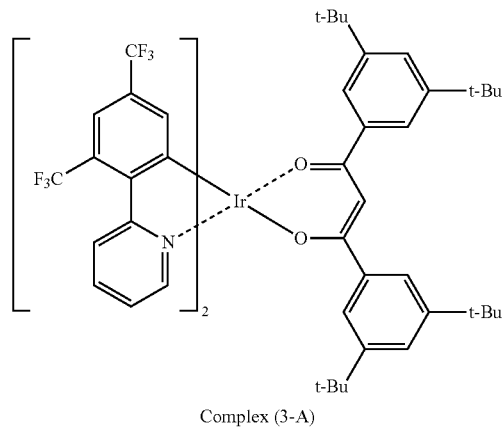

Complex (3-A)

Synthesis of Iridium Complex (3-A)

The precursor (3) (0.240 g, 0.149 mmol), 1,3-bis(3,5-di(tert-butyl)phenyl)propane-1,3-dione (β-diketone (A)), (0.129 g, 0.288 mmol) and sodium carbonate (1.91 g, 18.1 mmol) was added to 2-ethoxyethanol (50 mL), and the resulting mixture was stirred for 2 hours at 100° C. under a nitrogen atmosphere. After being allowed to cool, the solvent was distilled off by a rotary evaporator, and then chloroform was added to the residue. The obtained mixed solution was washed with water and a saturated saline, and was then dried by adding an appropriate amount of anhydrous sodium sulfate. After removal of the sodium sulfate by filtration, the solvent of the filtrate was distilled off with a rotary evaporator. The iridium complex 3-A was obtained in a yield of 44% (154 mg, 0.126 mmol) by purifying the obtained residue with a silica gel column chromatography (development solvent; chloroform:hexane=1:1 (v/v)), and by further performing recrystallization using methanol. The properties of the thus synthesized compound were as follows.

$^1$H NMR (CDCl$_3$): δ1.25 (s, 36H), 6.53 (s, 1H), 6.70 (s, 2H), 7.20-7.24 (m, 2H), 7.44 (d, J=2.0 Hz, 4H), 7.50 (t, J=2.0 Hz, 2H), 7.54 (s, 2H), 7.86-7.91 (m, 2H), 8.44 (d, J=8.0 Hz, 2H), 8.67 (dd, J=1.4 and 5.8 Hz, 2H)

ESI-TOF MS: m/z 1243 ([M+Na]$^+$)

Anal. Calcd for C$_{57}$H$_{55}$F$_{12}$IrN$_2$O$_2$: C, 56.10; H, 4.54; 2.30. Found: C, 56.27; H, 4.74; 2.41.

Synthesis of Iridium Complex (3-B)

In accordance with the following formula, the iridium complex 3-B was obtained by reacting the precursor (3) and the β-diketone (B) with each other.

[Chemical Formula 37]

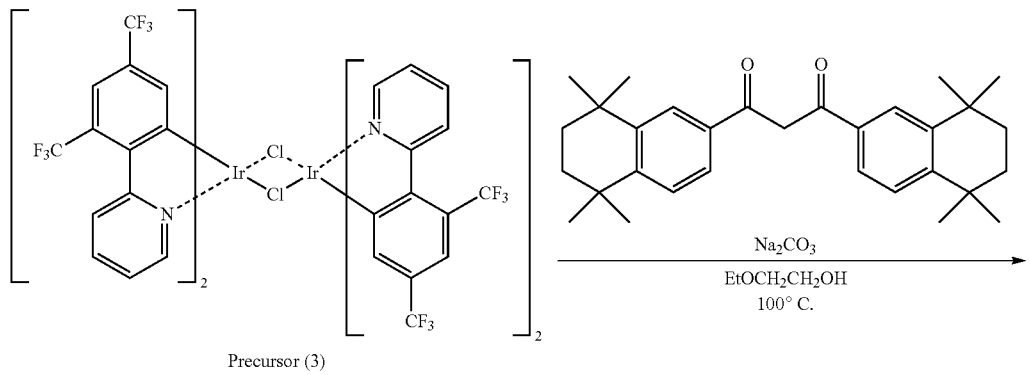

Precursor (3)

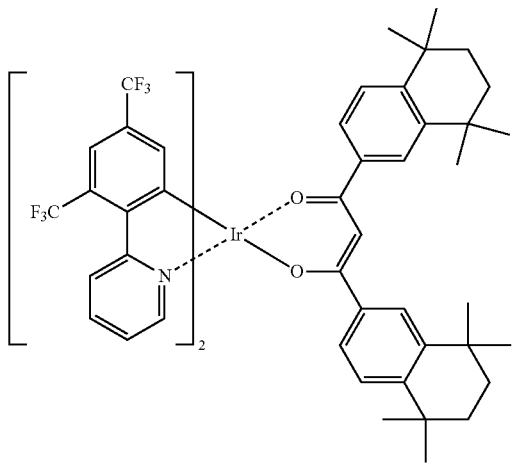

Complex (3-B)

Synthesis of Iridium Complex (3-B)

The precursor (3) (0.241 g, 0.149 mmol), β-diketone (B), (0.129 g, 0.290 mmol) and sodium carbonate (1.90 g, 18.0 mmol) was added to 2-ethoxyethanol (50 mL), and the resulting mixture was stirred for 2 hours at 100° C. under a nitrogen atmosphere. After being allowed to cool, the solvent was distilled off by a rotary evaporator, and then chloroform was added to the residue. The obtained mixed solution was washed with water and a saturated saline, and was then dried by adding an appropriate amount of anhydrous sodium sulfate. After removal of the sodium sulfate by filtration, the solvent of the filtrate was distilled off with a rotary evaporator. The iridium complex 2-B was obtained in a yield of 17% (59.7 mg, 0.0491 mmol) by purifying the obtained residue with a silica gel column chromatography (development solvent; chloroform:hexane=1:1 (v/v)), and by further performing recrystallization using methanol. The properties of the thus synthesized compound were as follows.

$^1$H NMR (CDCl$_3$): δ1.16 (s, 6H), 1.18 (s, 6H), 1.22 (s, 6H), 1.23 (s, 6H), 1.64 (s, 8H), 6.52 (s, 1H), 6.64 (s, 2H), 7.20 (t, J=6.0 Hz, 2H), 7.27 (d, J=7.8 Hz, 2H), 7.43 (dd, J=2.0 and 7.8 Hz, 2H), 7.53 (s, 2H), 7.61 (d, J=2.0 Hz, 2H), 7.83-7.88 (m, 2H), 8.41 (d, J=8.0 Hz, 2H), 8.63 (d, J=6.0 Hz, 2H)

ESI-TOF MS: m/z 1239 ([M+Na]$^+$)

Anal. Calcd for C$_{57}$H$_{51}$F$_{12}$IrN$_2$O$_2$: C, 56.29; H, 4.23; 2.30. Found: C, 56.30; H, 4.05; 2.28.

Synthesis of Iridium Complex (3-X)

In accordance with the following formula, the iridium complex 3-X was obtained by reacting the precursor (3) and the β-diketone (X) with each other.

[Chemical Formula 38]

Precursor (3)

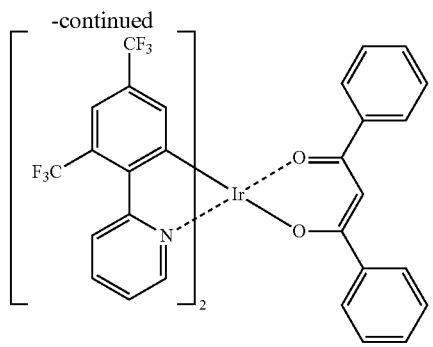

Complex (3-X)

Synthesis of Iridium Complex (3-X)

The precursor (3) (0.200 g, 0.124 mmol), β-diketone (X), (0.128 g, 0.571 mmol) and sodium carbonate (0.115 g, 1.09 mmol) was added to 2-ethoxyethanol (23 mL), and the resulting mixture was stirred for 3 hours at 105° C. under a nitrogen atmosphere. After being allowed to cool, the solvent was distilled off by a rotary evaporator, and then chloroform was added to the residue. The obtained mixed solution was washed with water and a saturated saline, and was then dried by adding an appropriate amount of anhydrous sodium sulfate. After removal of the sodium sulfate by filtration, the solvent of the filtrate was distilled off with a rotary evaporator. The iridium complex 3-X was obtained in a yield of 10% (25.0 mg, 0.0251 mmol) by purifying the obtained residue with a silica gel column chromatography (development solvent; chloroform), and by further performing recrystallization using methanol. The properties of the thus synthesized compound were as follows.

$^1$H NMR (CDCl$_3$): δ6.60 (s, 2H), 6.61 (s, 1H), 7.21-7.24 (m, 2H), 7.32 (t, J=7.4 Hz, 4H), 7.44 (t, J=7.4 Hz, 2H), 7.54 (s, 2H), 7.72 (d, J=7.4 Hz, 4H), 7.85-7.90 (m, 2H), 8.41 (d, J=8.8 Hz, 2H), 8.64 (dd, J=0.8 and 5.8 Hz, 2H)

ESI-TOF MS: m/z 1019 ([M+Na]$^+$)

Anal. Calcd for C$_{41}$H$_{23}$F$_{12}$IrN$_2$O$_2$: C, 49.45; H, 2.33; 2.81. Found: C, 49.60; H, 2.70; 2.70.

Synthesis of Iridium Complex (4-A)

In accordance with the following formula, the iridium complex 4-A was obtained by reacting the precursor (4) and the β-diketone (A) with each other.

[Chemical Formula 39]

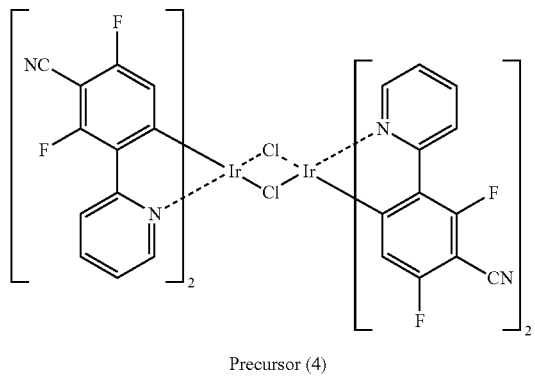

Precursor (4)

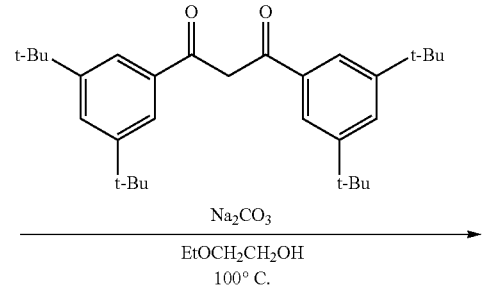

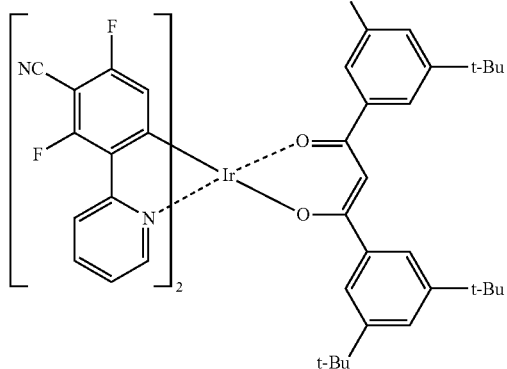

Complex (4-A)

Synthesis of Iridium Complex (4-A)

The precursor (4) (0.243 g, 0.185 mmol), 1,3-bis(3,5-di(tert-butyl)phenyl)propane-1,3-dione (β-diketone (A)), (0.133 g, 0.296 mmol) and sodium carbonate (1.90 g, 17.9 mmol) was added to 2-ethoxyethanol (50 mL), and the resulting mixture was stirred for 2 hours at 100° C. under a nitrogen atmosphere. After being allowed to cool, the solvent was distilled off by a rotary evaporator, and then ethyl acetate was added to the residue. The obtained mixed solution was washed with water and a saturated saline, and was then dried by adding an appropriate amount of anhydrous magnesium sulfate. After removal of the magnesium sulfate by filtration, the solvent of the filtrate was distilled off with a rotary evaporator. The iridium complex 4-A was obtained in a yield of 12% (0.0459 g, 0.0429 mmol) by purifying the obtained residue with a silica gel column chromatography (development solvent; chloroform), and by further performing recrystallization using methanol. The properties of the thus synthesized compound were as follows.

$^1$H NMR (CDCl$_3$): δ 1.26 (s, 36H), 5.98 (d, J=8.6 Hz, 2H), 6.56 (s, 1H), 7.22 (td, J=1.4 and 5.9 Hz, 2H), 7.49 (d, J=1.8 Hz, 4H), 7.54 (t, J=1.8 Hz, 2H), 7.90 (td, J=1.4 and 8.2 Hz, 2H), 8.32 (d, J=8.2 Hz, 2H), 8.55 (dd, J=1.4 and 5.9 Hz, 2H)

ESI-TOF MS: m/z 1093 ([M+Na]$^+$)

Anal. Calcd for C$_{55}$H$_{53}$F$_4$IrN$_4$O$_2$: C, 61.72; H, 4.99; N, 5.23. Found: C, 61.72; H, 5.03; N, 5.23.

Synthesis of Iridium Complex (4-B)

In accordance with the following formula, the iridium complex 4-B was obtained by reacting the precursor (4) and the β-diketone (B) with each other.

[Chemical Formula 37]

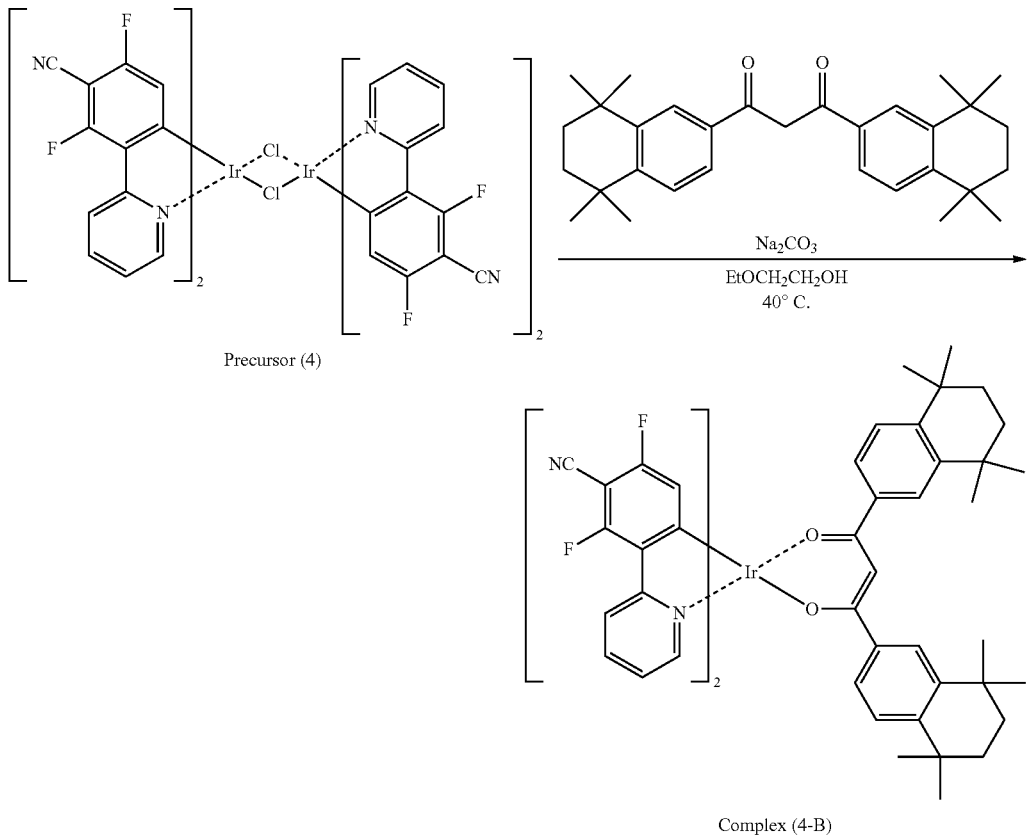

Precursor (4)

Complex (4-B)

Synthesis of Iridium Complex (4-B)

The precursor (4) (0.106 g, 0.0805 mmol), β-diketone (B), (0.0884 g, 0.199 mmol) and sodium carbonate (0.0531 g, 0.501 mmol) was added to 2-ethoxyethanol (25 mL), and the resulting mixture was stirred for 1 hour and 30 minutes at 40° C. under a nitrogen atmosphere. After being allowed to cool, the solvent was distilled off by a rotary evaporator, and then methylene chloride was added to the residue. The obtained mixed solution was washed with water and a saturated saline, and was then dried by adding an appropriate amount of anhydrous magnesium sulfate. After removal of the magnesium sulfate by filtration, the solvent of the filtrate was distilled off with a rotary evaporator. The iridium complex 4-B was obtained in a yield of 22% (0.0378 g, 0.0355 mmol) by purifying the obtained residue with a silica gel column chromatography (development solvent; methylene chloride), and by further performing recrystallization using methanol. The properties of the thus synthesized compound were as follows.

$^1$H NMR (CDCl$_3$): δ1.24 (m, 24H), 1.66 (m, 8H), 5.92 (d, J=8.6 Hz, 2H), 6.58 (s, 1H), 7.21-7.24 (m, 2H), 7.29 (d, J=8.6 Hz, 2H), 7.48 (dd, J=1.8 and 8.6 Hz, 2H), 7.69 (d, J=1.8 Hz, 2H), 7.86-7.90 (m, 2H), 8.30 (d, J=8.6 Hz, 2H), 8.50 (dd, J=1.4 and 5.9 Hz, 2H)

ESI-TOF MS: m/z 1089 ([M+Na]$^+$)

Anal. Calcd for $C_{55}H_{49}F_4IrN_4O_2$: C, 61.96; H, 4.63; N, 5.25. Found: C, 61.94; H, 4.59; N, 5.25.

Synthesis of Iridium Complex (4-X)

In accordance with the following formula, the iridium complex 4-X was obtained by reacting the precursor (4) and the β-diketone (X) with each other.

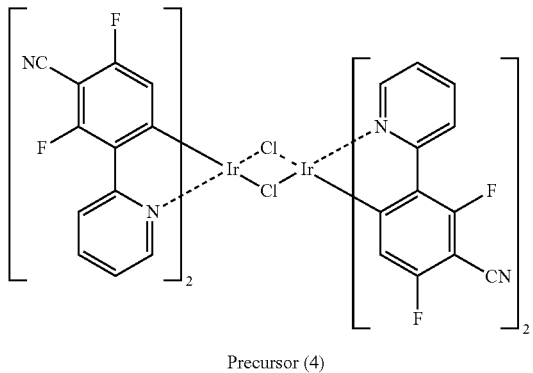

Precursor (4)

[Chemical Formula 41]

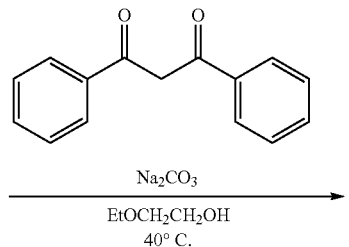

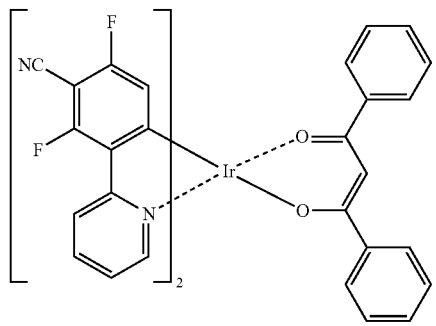

Complex (4-X)

Synthesis of Iridium Complex (4-X)>

The precursor (4) (0.0980 g, 0.0745 mmol), β-diketone (X), (0.0496 g, 0.221 mmol) and sodium carbonate (0.0650 g, 0.613 mmol) was added to 2-ethoxyethanol (7 mL), and the resulting mixture was stirred for 30 minutes at 40° C. under a nitrogen atmosphere. After being allowed to cool, the solvent was distilled off by a rotary evaporator, and then methylene chloride was added to the residue. The obtained mixed solution was washed with water and a saturated saline, and was then dried by adding an appropriate amount of anhydrous magnesium sulfate. After removal of the magnesium sulfate by filtration, the solvent of the filtrate was distilled off with a rotary evaporator. The iridium complex 4-X was obtained in a yield of 21% (0.0254 g, 0.0300 mmol) by purifying the obtained residue with a silica gel column chromatography (development solvent; methylene chloride), and by further performing recrystallization using methanol. The properties of the thus synthesized compound were as follows.

$^1$H NMR (CDCl$_3$): δ5.91 (d, J=8.8 Hz, 2H), 6.65 (s, 1H), 7.26-7.28 (m, 2H), 7.35 (t, J=7.7 Hz, 4H), 7.45-7.49 (m, 2H), 7.75-7.77 (m, 4H), 7.90 (td, J=1.4 and 8.4 Hz, 2H), 8.32 (d, J=8.4 Hz, 2H), 8.49 (dd, J=1.4 and 5.6 Hz, 2H)

ESI-TOF MS: m/z 869 ([M+Na]$^+$)

Anal. Calcd for $C_{39}H_{21}F_4IrN_4O_2$: C, 55.38; H, 2.50; N, 6.62. Found: C, 55.38; H, 2.74; N, 6.74.

[Evaluation of Photoluminescence (PL) Spectrum and PL Quantum Yield]

The photoluminescence (PL) spectrum and the PL quantum yield $\varphi_{PL}$ of each iridium complex obtained above were measured. Fluorolog-3 spectrometer manufactured by HORIBA, Ltd. was used for measuring the PL spectrum. C9920-12 Quantum yield measuring machine manufactured by HAMAMATSU Photonics K.K. was used for measuring the PL quantum yield. The evaluation of these PL spectrum and PL quantum yield were conducted in a polymer thin film (polymethyl methacrylate, PMMA), as medium. Note that the solution sample sealed with argon gas was measured as a deoxidized solution, and the polymer thin film sample was measured under a nitrogen atmosphere. The polymer thin film sample was measured by 0.05 mmol/g (4 wt %) doping of each iridium complex into PMMA. The results are shown in the following Table.

TABLE 1

|  | Wavelength $\lambda_{PL}$ (nm) | PL Quantum yield $\varphi_{PL}$ |
|---|---|---|
| 1-A | 537 | 0.58 |
| 2-A | 545 | 0.52 |
| 3-A | 545 | 0.49 |
| 4-A | 543 | 0.45 |
| 1-B | 537 | 0.62 |
| 2-B | 548 | 0.47 |
| 3-B | 548 | 0.68 |
| 4-B | 537 | 0.53 |
| 1-X | 550 | 0.23 |
| 2-X | 561 | 0.17 |

From the above Table, the iridium complexes having the tert-butyl-substituted phenyl group as the β-diketone (1-A, 2-A, 3-A, 4-A, 1-B, 2-B, 3-B, 4-B) showed photoluminescence quantum yields higher than 0.45 in the polymer thin film.

Next, with respect to the iridium complexes 1-A, 2-A, 1-B, 2-B, the PL spectrum and PL quantum yield were evaluated in an organic solvent (dichloromethane ($CH_2Cl_2$)), as medium. The results are shown in the following Table and in FIG. 1. In the following Table, the results in the polymer thin film are shown together, and also calculated values of difference (wavelength shift $\Delta\lambda_{PL}$) between the position of wavelength peak in the organic solvent and the position of wavelength peak in the polymer thin film are shown.

TABLE 2

|     | In organic solvent | | In polymer thin film | | Wavelength shift |
| --- | --- | --- | --- | --- | --- |
|     | $\lambda_{PL}$ (nm) | $\varphi_{PL}$ | $\lambda_{PL}$ (nm) | $\varphi_{PL}$ | $\Delta\lambda_{PL}$ |
| 1-A | 573 | 0.19 | 537 | 0.58 | 36 |
| 2-A | 595 | 0.11 | 545 | 0.52 | 50 |
| 1-B | 567 | 0.28 | 537 | 0.62 | 30 |
| 2-B | 596 | 0.18 | 548 | 0.47 | 48 |

From the above Table and FIG. 1, with respect to the iridium complexes having the tert-butyl-substituted phenyl group as the β-diketone (1-A, 2-A, 1-B, 2-B), the rigidchromism was observed where the position of the wavelength peak in the polymer thin film shifted to the short wavelength side relative to the wavelength peak in an organic solvent. In the viewpoint of luminescent color, the light emission wavelength of yellowish green to orange in the organic solvent changed to the light emission wavelength of green to yellow in the polymer thin film.

From the aforementioned results, it has been found that the iridium complexes having the tert-butyl-substituted phenyl group as the β-diketone had the PL quantum yield $\varphi_{PL}$ of 0.45 or more when doping to the polymer thin film at a dose of 0.05 mmol, and showed the rigidchromism where the light emission wavelength in the polymer thin film shifted to the short wavelength side relative to the light emission wavelength in an organic solvent.

[Production and Property Evaluation of Organic EL Element]

Figure 2:
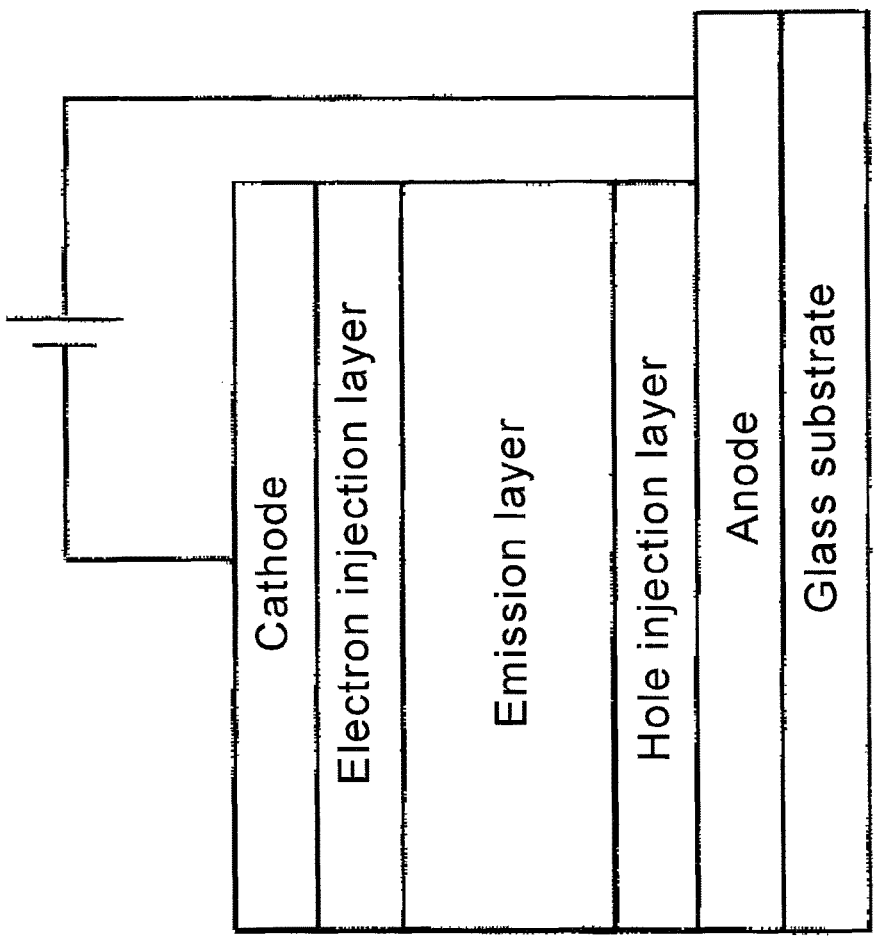
FIG. 2 is a cross-sectional schematic view of the organic EL element produced in the embodiment.

The iridium complexes were used to produce the organic EL element (1) shown in FIG. 2 in the following procedures, and its properties were evaluated.

<Production of Organic EL Element>

(a) Formation of Hole Injection Layer (5)

An anode (2) was prepared by subjecting an ITO-glass substrate (manufactured by SANYO Vacuum Industries Co., Ltd., ITO, film thickness 150 nm) to patterning treatment and then by performing washing. Next, the ITO thin film was surface-treated by ozone. After the surface treatment, a hole injection layer (5) having a thickness of 40 nm was formed by rapid film formation of a hole injection material on the ITO film through the use of the spin coating method, and by baking at 120° C. for 1 hour. An electrically conductive polymer (P VP CH8000 manufactured by Heraeus Clevios) containing PEDOT and PSS was used as the hole injection material.

(b) Formation of Emission Layer (4)

An ink Ink (1-A) for the emission layer was prepared by dissolution of poly(9-vinylcarbasol) (PVCz, manufactured by Sigma-Aldrich, Number average molecular weight Mn, 25000-50000, purified by re-precipitating from THF-methanol), 2-(4-biphenilyl)-5-(4-tert-butylphenyl)-1,3,4-oxadiazole (PBD) and the iridium complex 1-A in a dehydrated toluene, and by filtration with a membrane filter (0.2 μm Millex-FG manufactured by Merck Millipore Corporation). The concentrations of the PBD and the iridium complex to be doped to 1 g of PVCz were 850 μmol and 98 μmol, respectively, and 0.7 ml of the toluene was used to 10 mg of PVCz as a solvent for the ink. Through the use of the obtained ink (1-A) for the emission layer, a emission layer 4 having a thickness of 80 nm was formed on the hole injection layer (5) by film formation using the spin coating method, and then by baking at 120° C. for 1 hour.

(c) Formation of Electron Injection Layer (6) and Cathode (3)

A thin film of cesium fluoride (electron injection layer (6), thickness 1 nm) as the electron-injecting material was formed by the vacuum deposition, through the use of a shadow mask, and then, a thin film of aluminum (cathode (3), thickness 250 nm) was produced. At this time, the electron injection layer (6) and the cathode (3) were produced so that the area of the light-emitting portion was 10 $mm^2$ (2 mm×5 mm). In this way, the organic EL element EL(1-A) was completed.

<Production of Organic EL Element Used Each Iridium Complex as Emitting Material>

An ink Ink (2-A) for the emission layer was prepared by using the iridium complex 2-A instead of the iridium complex 1-A. An organic EL element EL(2-A) was obtained in the similar way to the above procedures except that the ink Ink (2-A) was used for the emission layer. The organic EL elements EL(3-A), EL(4-A), EL(1-B), EL(2-B), EL(3-B), EL(4-B), EL(1-X), EL(2-X), EL(3-X), EL(4-X) were also produced by using the complexes 3-A, 4-A, 1-B, 2-B, 3-B, 4-B, 1-X, 2-X, 3-X, 4-X instead of the complex 1-A.

<Evaluation of Organic EL Element Properties>

Samples for evaluating the organic EL properties were produced with the organic EL element obtained by the above steps sealed into a cavity glass by using an ultraviolet curable resin.

The organic EL element properties such as EL spectrum, maximum luminance $L_{max}$ ($cd/m^2$), maximum external quantum efficiency $\eta_{ext.max}$ (%), and CIE standard colorimetric system (x,y) were measured by a luminance goniophotometer (C-9920-11, manufactured by HAMAMATSU Photonics K.K.).

Table 2 shows the results of the peak wavelength $\lambda_{EL}$ (nm), the maximum luminance $L_{max}$ ($cd/m^2$), the maximum external quantum efficiency $\eta_{ext.max}$ (%), the maximum current efficiency $\eta_{j,max}$ (cd/A), the maximum power efficiency $\eta_{p,max}$ (lm/W), and CIE standard colorimetric system (x,y). The $L_{max}$ and $\eta_{ext.max}$ are shown along with the applied voltage (V) at the time of measurement in brackets. Note that the luminescence starting voltage $V_{turn-on}$ represents the voltage at which the luminance reaches 1 $cd/m^2$.

Figure 3A:
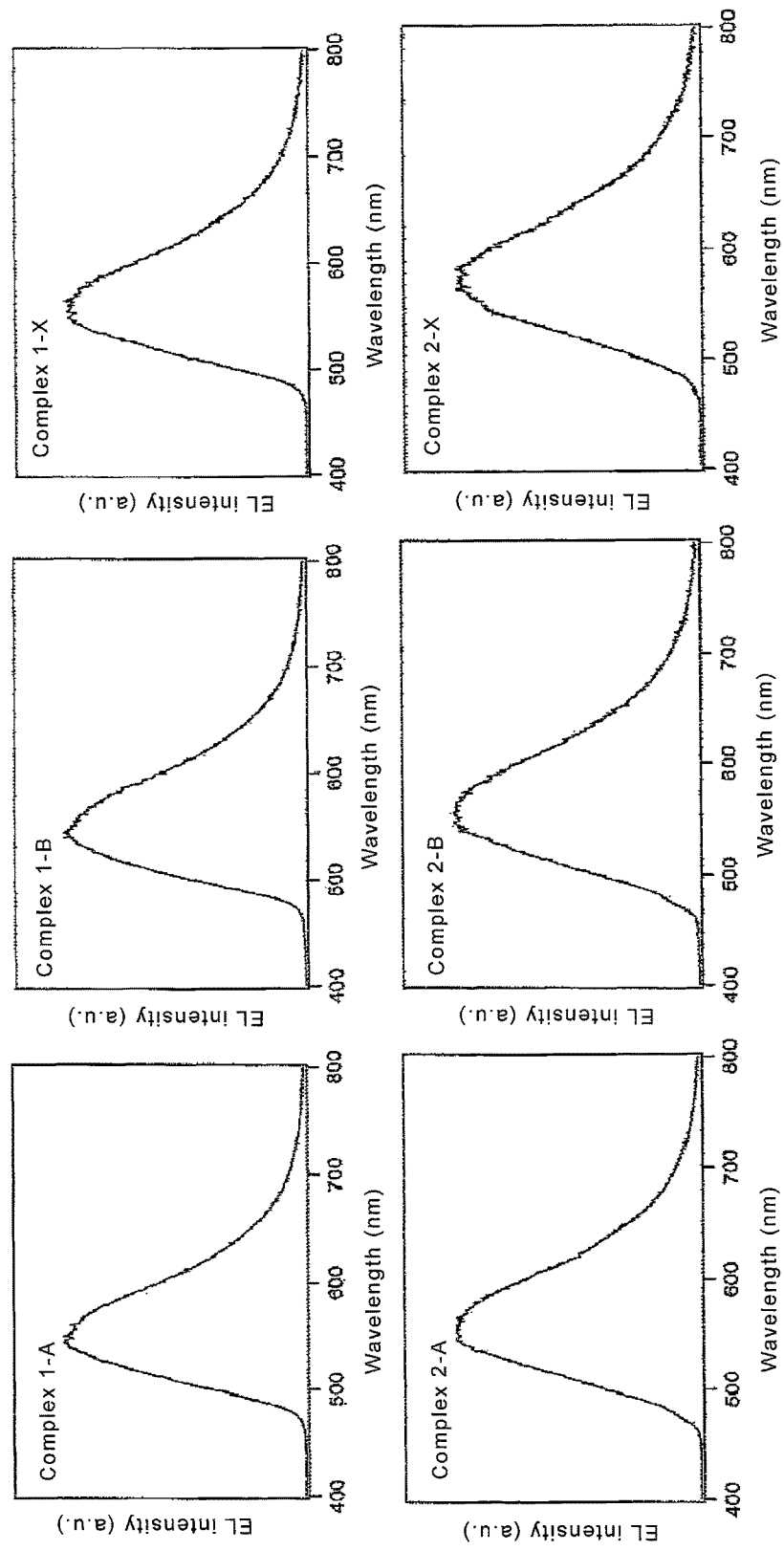
FIG. 3A and FIG. 3B shows the results of the light emission property of the organic EL element according to the embodiment.
Figure 3B:
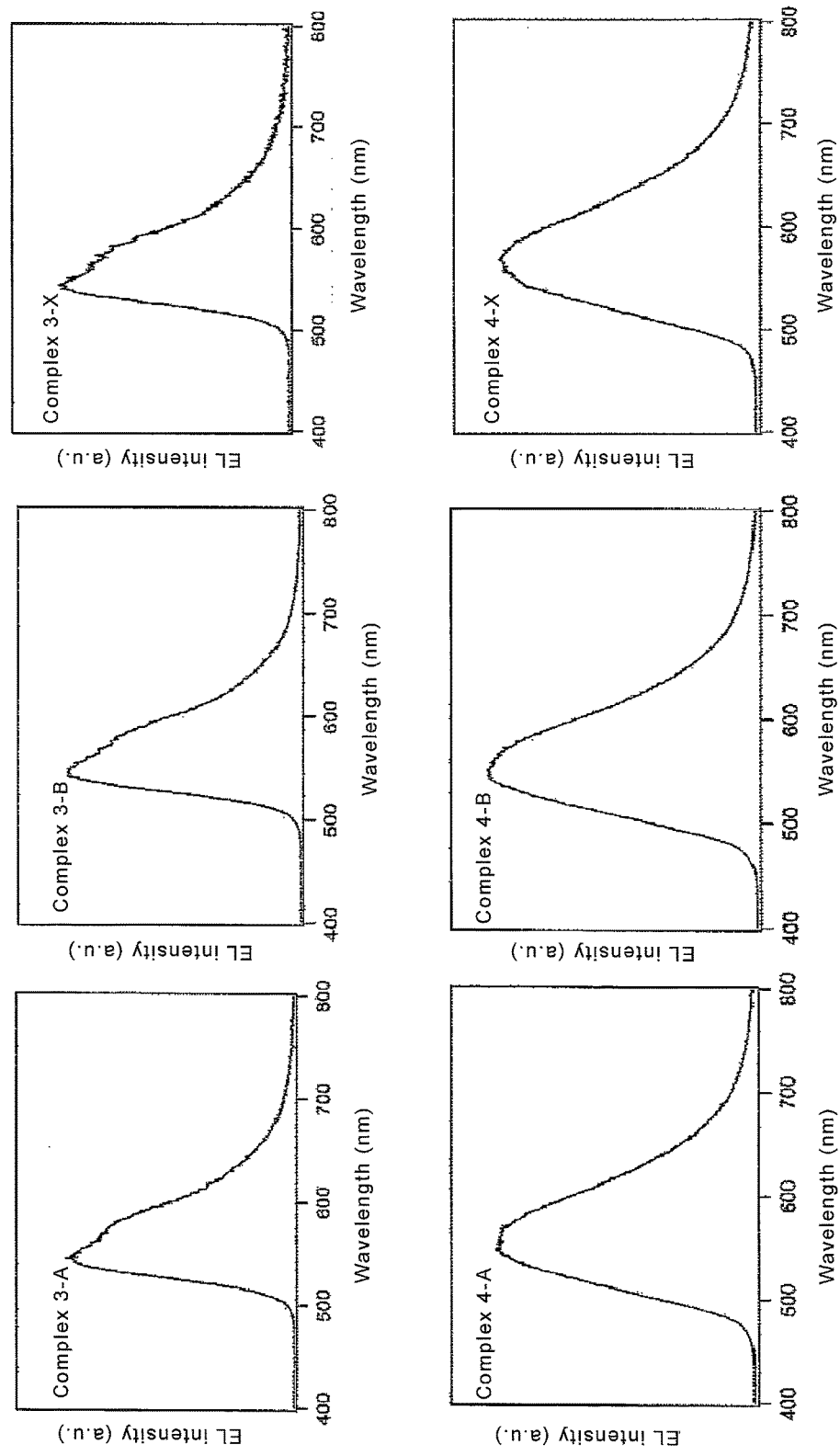

Furthermore, FIG. 3A and FIG. 3B shows the electroluminescent (EL) spectrum of the organic EL element EL(1-A), EL(2-A), EL(3-A), EL(4-A), EL(1-B), EL(2-B), EL(3-B), EL(4-B), EL(1-X), EL(2-X), EL(3-X), EL(4-X). The EL spectrum was measured at the maximum luminance $L_{max}$.

TABLE 3

| Element | Luminescence starting voltage $V_{turn-on}$/V | Maximum luminance $L_{max}$/cd m$^{-2}$ (@V) | Maximum external quantum efficiency $\eta_{ext.\,max}$/% (@V) | Maximum current efficiency $\eta_{j,\,max}$/cd A$^{-1}$ (@V) | Maximum power efficiency $\eta_{p,\,max}$/lm W$^{-1}$ (@V) | $\lambda_{EL}$/nm | CIE (x, y) |
|---|---|---|---|---|---|---|---|
| EL (1-A) | 4.0 | 6200 (14.0) | 3.0 (8.5) | 9.5 (8.5) | 4.1 (7.0) | 550 | (0.43, 0.54) |
| EL (1-B) | 4.5 | 4500 (15.0) | 1.8 (8.0) | 5.8 (6.5) | 3.8 (4.5) | 539 | (0.42, 0.54) |
| EL (1-X) | 5.0 | 2900 (15.0) | 1.3 (9.5) | 4.0 (9.5) | 1.2 (7.0) | 564 | (0.45, 0.53) |
| EL (2-A) | 4.0 | 4900 (14.0) | 1.7 (9.5) | 5.1 (9.5) | 1.8 (8.0) | 555 | (0.44, 0.52) |
| EL (2-B) | 4.5 | 3200 (15.5) | 1.5 (9.5) | 4.3 (11.0) | 1.4 (9.5) | 555 | (0.44, 0.52) |
| EL (2-X) | 5.5 | 1500 (15.0) | 0.51 (9.0) | 1.4 (8.5) | 0.58 (7.0) | 568 | (0.48, 0.50) |
| EL (3-A) | 6.0 | 2700 (17.0) | 1.1 (11.5) | 3.7 (11.5) | 1.1 (10.0) | 545 | (0.46, 0.53) |
| EL (3-B) | 5.0 | 3700 (15.5) | 1.2 (10.0) | 4.1 (11.0) | 1.2 (10.0) | 543 | (0.46, 0.53) |
| EL (3-X) | 8.5 | 1000 (18.0) | 0.37 (12.5) | 1.3 (12.5) | 0.31 (12.5) | 545 | (0.46, 0.53) |
| EL (4-A) | 4.0 | 8300 (15.5) | 2.9 (10.5) | 9.4 (9.5) | 3.1 (9.5) | 549 | (0.42, 0.54) |
| EL (4-B) | 4.0 | 11000 (15.0) | 2.9 (10.0) | 9.0 (10.0) | 2.8 (10.0) | 551 | (0.41, 0.54) |
| EL (4-X) | 3.5 | 4400 (15.5) | 1.1 (11.0) | 3.1 (11.0) | 0.98 (9.0) | 569 | (0.45, 0.52) |

From the above results, the organic EL elements produced by using complexes 1-A, 2-A, 3-A, 4-A, 1-B, 2-B, 3-B, and 4-B exhibit improved organic EL properties in comparison with the organic EL elements produced by using the complexes 1-X, 2-X, 3-X, and 4-X.

INDUSTRIAL APPLICABILITY

The organoiridium complex of the present invention is suitable as a emitting material of the organic EL element because of high photoluminescence quantum yield in the polymer thin film. Particularly, the present invention is suitable as a yellow to green emitting material.

The invention claimed is:

1. An organoiridium complex for an organic electroluminescent element represented by Chemical Formula 1, wherein a C—N ligand comprising two atomic groups (A$^1$, A$^2$), and a β-diketone ligand in line symmetry having two tert-butyl-substituted phenyl groups are coordinated with an iridium atom,

[Chemical Formula 1]

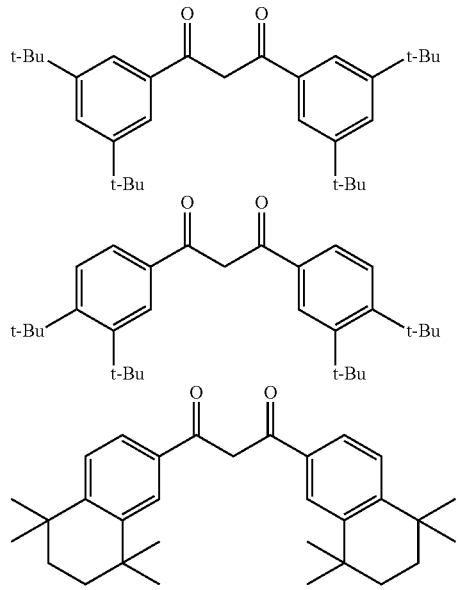

wherein R$^1$, R$^2$, and R$^3$ are each a tert-butyl group or a hydrogen atom, and two of R$^1$, R$^2$, and R$^3$ are a tert-butyl group, and each phenyl ring of the β-diketone is substituted with the two tert-butyl groups, wherein the two tert-butyl groups may bond each other to thereby form a saturated hydrocarbon ring, and wherein the β-diketone ligand is represented by any of the formula in Chemical Formula 2;

[Chemical Formula 2]

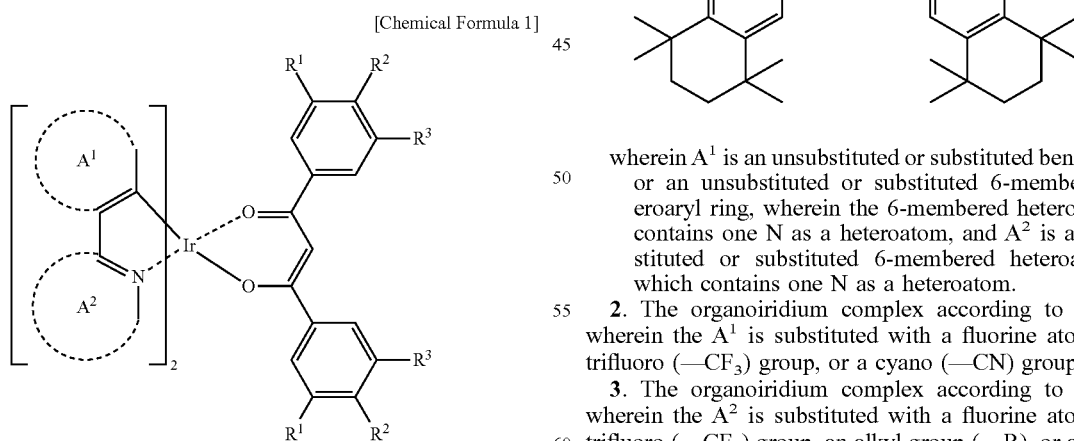

wherein A$^1$ is an unsubstituted or substituted benzene ring or an unsubstituted or substituted 6-membered heteroaryl ring, wherein the 6-membered heteroaryl ring contains one N as a heteroatom, and A$^2$ is an unsubstituted or substituted 6-membered heteroaryl ring which contains one N as a heteroatom.

2. The organoiridium complex according to claim 1, wherein the A$^1$ is substituted with a fluorine atom (F), a trifluoro (—CF$_3$) group, or a cyano (—CN) group.

3. The organoiridium complex according to claim 1, wherein the A$^2$ is substituted with a fluorine atom (F), a trifluoro (—CF$_3$) group, an alkyl group (—R), or an alkoxy group (—OR).

4. The organoiridium complex according to claim 1, wherein a PL quantum yield $\Phi_{PL}$ when 0.05 mmol/g doping is performed in a polymer thin film is 0.45 or more.

5. The organoiridium complex according to claim 1, wherein the light emission wavelength ($\lambda_{PL}$) in the polymer thin film is 510 nm or more and 580 nm or less.

6. An organic electroluminescent element having an emission layer including the organoiridium complex according to claim 1.

7. The organoiridium complex according to claim 2, wherein the $A^2$ is substituted with a fluorine atom (F), a trifluoro (—$CF_3$) group, an alkyl group (—R), or an alkoxy group (—OR).

\* \* \* \* \*